(12) United States Patent
Furgeson et al.

(10) Patent No.: US 7,863,470 B2
(45) Date of Patent: Jan. 4, 2011

(54) LINEAR POLYETHYLENIMINE-STEROL CONJUGATES FOR GENE DELIVERY

(75) Inventors: Darin Y. Furgeson, Salt Lake City, UT (US); Sung Wan Kim, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 823 days.

(21) Appl. No.: 11/711,933

(22) Filed: Feb. 27, 2007

(65) Prior Publication Data

US 2007/0154447 A1      Jul. 5, 2007

Related U.S. Application Data

(62) Division of application No. 10/623,020, filed on Jul. 17, 2003, now Pat. No. 7,183,263.

(60) Provisional application No. 60/396,966, filed on Jul. 17, 2002.

(51) Int. Cl.
   *C07J 9/00*     (2006.01)
(52) U.S. Cl. .................................... 552/544
(58) Field of Classification Search .................. 552/544
   See application file for complete search history.

(56) References Cited

U.S. PATENT DOCUMENTS 3,795,667 A * 3/1974 Ondetti ..................... 530/323
5,536,745 A * 7/1996 Pearson ..................... 514/460
5,783,565 A    7/1998 Lee et al.
5,935,936 A    8/1999 Fasbender et al.

FOREIGN PATENT DOCUMENTS

WO    WO 01/57064    *    8/2001

OTHER PUBLICATIONS

D.Y. Fergeson, R.n. Cohen, R.I. Mahato & S.W. Kim, Novel Water Insuluble Lipoparticulates for Gene Delivery, 19 Pharm. Res. 382-390 (2002).
Affleck, D.G., Yu, L., Bull, D.A.,Bailey, S.H., & Kim, S.W., Augmentation of myocardial transfection using Terplex DNA: a novel gene delivery system, 8 GeneTher. 349-353 (2001).
Lee, M., Rentz, J., Han, S.O., Bull, D.A., & Kim, S.W., Water-soluble lipopolymer as an efficient carrier for gene delivery to myocardium, 10 Gene Ther. 585-593 (2003).

* cited by examiner

*Primary Examiner*—Barbara P Badio
(74) *Attorney, Agent, or Firm*—Clayton, Howarth & Cannon, P.C.

(57) ABSTRACT

Linear polyethylenimine was modified with sterols, such as cholesterol, in three different geometries: linear shaped (L), T-shaped (T), and a combined linear- and T-shaped (LT), to result in linear polyethylenimine-sterol conjugates. These conjugates were mixed with nucleic acids to form complexes for delivery of the nucleic acids into cells. Mammalian cells transfected with these complexes showed protein expression levels higher than linear polyethylenimine alone, and twice that of branched polyethylenimine, but without any significant loss in cell viability. Methods of making these compositions and methods of using them for gene delivery are also described.

18 Claims, 13 Drawing Sheets

LINEAR POLYETHYLENIMINE-STEROL CONJUGATES FOR GENE DELIVERY

CROSS-REFERENCE TO RELATED APPLICATIONS

This application is a division of U.S. application Ser. No. 10/623,020, filed Jul. 17, 2003, now U.S. Pat. No. 7,183,263, which claims the benefit of U.S. Provisional Application No. 60/396,966, filed Jul. 17, 2002, both of which are hereby incorporated by reference.

STATEMENT REGARDING FEDERALLY SPONSORED RESEARCH OR DEVELOPMENT

Not applicable.

BACKGROUND OF THE INVENTION

This invention relates to gene delivery. More particularly, this invention relates to linear polyethylenimine-sterol conjugates as carriers for gene delivery.

Polyethylenimine (PEI) has long been used as a carrier for non-viral gene delivery, however, the ideal molecular weight and geometry of PEI for gene delivery have not been determined. A. von Harpe et al., 69 J. Control. Release 309-322 (2000). Typical molecular weights of PEI vary from about 423 to about 800,000, with linear and branched geometries. Linear PEI (LPEI) (MW 423) cannot efficiently buffer the low pH found in the secondary lysosome after endocytosis. Consequently, the need for a co-lipid to facilitate the release of plasmid DNA (pDNA) has been shown. D. Y. Furgeson, R. N. Cohen, R. I. Mahato & S. W. Kim, 19 Pharm. Res. 382-390 (2002). However, LPEI (MW 25,000) has over 520 secondary amines capable of protonation and subsequent pH buffering. Therefore, the higher molecular weight polymers do not require a co-lipid for release of plasmid DNA from endosomes. LPEI has been shown to be an effective non-viral gene carrier, D. Goula et al., 5 Gene Ther. 712-717 (1998); J. L. Coll et al., 10 Hum. Gene Ther. 1659-1666 (1999); P. Chollet et al., 4 J. Gene Med. 84-91 (2002); D. Goula et al., 7 Gene Ther. 499-504 (2000); S. M. Zou et al., 2 J. Gene Med. 128-134 (2000); A. N. Uduehi et al., 4 Mol. Ther. 52-57 (2001); L. Wightman et al., 3 J. Gene Med. 362-372 (2001); S. Brunner et al., 5 Mol. Ther. 80-86 (2002); R. Kircheis et al., 9 Cancer Gene Ther. 673-680 (2002), with increased gene expression and decreased toxicity compared to branched PEI (BPEI). The putative method of PEI gene expression is through endosomal release by osmotic swelling by the proton sponge effect. O. Boussif et al., 92 Proc. Nat'l Acad. Sci. USA 7297-7301 (1995).

Thus, while prior art gene carriers are known and are generally suitable for their limited purposes, they possess certain inherent deficiencies that detract from their overall utility for gene delivery.

In view of the foregoing, it will be appreciated that providing linear polyethylenimine-sterol conjugates as gene carriers would be a significant advancement in the art.

BRIEF SUMMARY OF THE INVENTION

An illustrative embodiment of the present invention comprises a composition of matter, i.e., an L-shaped linear polyethylenimine sterol conjugate, having a formula represented by

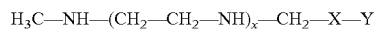

wherein x is an integer of about 8 to about 1,200, X is a linker, and Y is a residue of a sterol comprising a 3-ol group.

In one illustrative embodiment of this composition, x is about 581, such that the LPEI portion of the composition has a molecular weight of about 25,000. An illustrative linker (X) is a —O—CO— group. Illustrative sterols include cholesterol, cholestanol, coprosterol, epicholestanol, epicholesterol, ergostanol, α-ergosterol, β-ergostenol, γ-ergostenol, ergosterol, 22,23-dihydroergosterol, stigmasterol, stigmastanol, (3β)-7-dehydrocholesterol, desmosterol, allocholesterol, 24-hydroxycholesterol, 25-hydroxycholesterol, campesterol, α₁-sitosterol, β-sitosterol, γ-sitosterol, lumisterol, pyrocalciferol, isopyrocalciferol, azacosterol, neoergosterol, dehydroergosterol, and the like. A typical sterol that can be used in this composition is cholesterol (LPC-L).

Another illustrative composition according to the present invention, i.e., a T-shaped linear polyethylenimine sterol conjugate, has a formula represented by

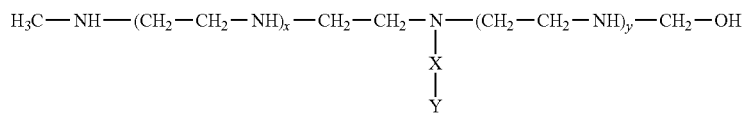

wherein x is an integer of about 0 to about 1,200, y is an integer of about 0 to about 1,200, with the proviso that x+y is about 8 to about 1,200, X is a linker, and Y is a residue of a sterol comprising a 3-ol group.

In one illustrative embodiment of this composition, x+y is about 581, such that the LPEI portion of the composition has a molecular weight of about 25,000. An illustrative liner (X) according to this composition is a —CO— group. A typical sterol (Y) in this composition is cholesterol (LPC-T).

Still another illustrative composition according to the present invention, i.e., an LT-shaped linear polyethylenimine sterol conjugate, has a formula represented by

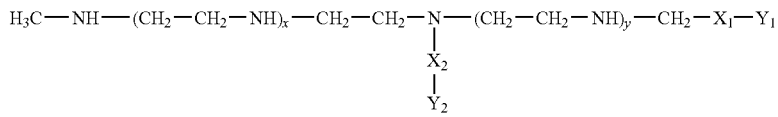

wherein x is an integer of about 0 to about 1,200, y is an integer of about 0 to about 1,200, with the proviso that x+y is about 8 to about 1,200, $X_1$ and $X_2$ are linkers, and $Y_1$ and $Y_2$ are residues of a sterol comprising a 3-ol group.

Illustrative linkers in this embodiment include where $X_1$ is a —O—CO— group and $X_2$ is a —CO— group. Typical embodiments include compositions wherein $Y_1$ and $Y_2$ are cholesterol residues (LPC-LT).

Yet another illustrative embodiment of the present invention comprises a complex comprising a mixture of a nucleic acid and one or more of the linear polyethylenimine sterol compositions described above.

Another illustrative embodiment of the invention comprises a method of making an L-shaped linear polyethylenimine sterol conjugate comprising reacting a linear polyethylenimine, having an average molecular weight of about 423 to about 50,000 and comprising a terminal hydroxyl group, with a chloroformate ester of a sterol comprising a 3-ol group, thereby resulting in the L-shaped linear polyethylenimine sterol conjugate comprising the sterol covalently bonded to the terminal hydroxyl group.

Still another illustrative embodiment of the invention comprises a method of making a T-shaped linear polyethylenimine sterol conjugate comprising:

(a) reacting a linear polyethylenimine, having an average molecular weight of about 423 to about 50,000 and comprising a terminal hydroxyl group and a plurality of secondary amine nitrogen atoms, with a protecting reagent such that the protecting reagent bonds with the terminal hydroxyl group, resulting in a protected linear polyethylenimine;

(b) reacting a chloroformate ester of a sterol comprising a 3-ol group with the protected linear polyethylenimine such that the chloroformate ester of a sterol bonds with at least one of the plurality of secondary amine nitrogen atoms, resulting in a protected T-shaped linear polyethylenimine sterol conjugate; and (c) deprotecting the protected T-shaped linear polyethylenimine sterol conjugate with a deprotecting reagent, resulting in the T-shaped linear polyethylenimine sterol conjugate.

An illustrative protecting reagent and an illustrative deprotecting reagent comprise chlorotrimethylsilane and trifluoroacetic acid, respectively.

Yet another illustrative embodiment of the present invention comprises a method of making an LT-shaped linear polyethylenimine sterol conjugate comprising reacting a linear polyethylenimine, having an average molecular weight of about 423 to about 50,000 and comprising a terminal hydroxyl group and a plurality of secondary amine nitrogen atoms, with a chloroformate ester of a sterol comprising a 3-ol group such that chloroformate ester of a sterol bonds with the terminal hydroxyl group and at least one of the plurality of secondary amine nitrogen atoms, thereby resulting in the LT-shaped linear polyethylenimine sterol conjugate.

Another illustrative embodiment according to the present invention comprises a method of delivering a nucleic acid into a mammalian cell comprising:

(a) mixing the nucleic acid with an L-shaped, T-shaped, or LT-shaped linear polyethylenimine sterol conjugate to result in a complex;

(b) contacting the mammalian cell with the complex such that the complex enters the mammalian cell, thereby delivering the nucleic acid into the mammalian cell.

DETAILED DESCRIPTION

Figure 1:
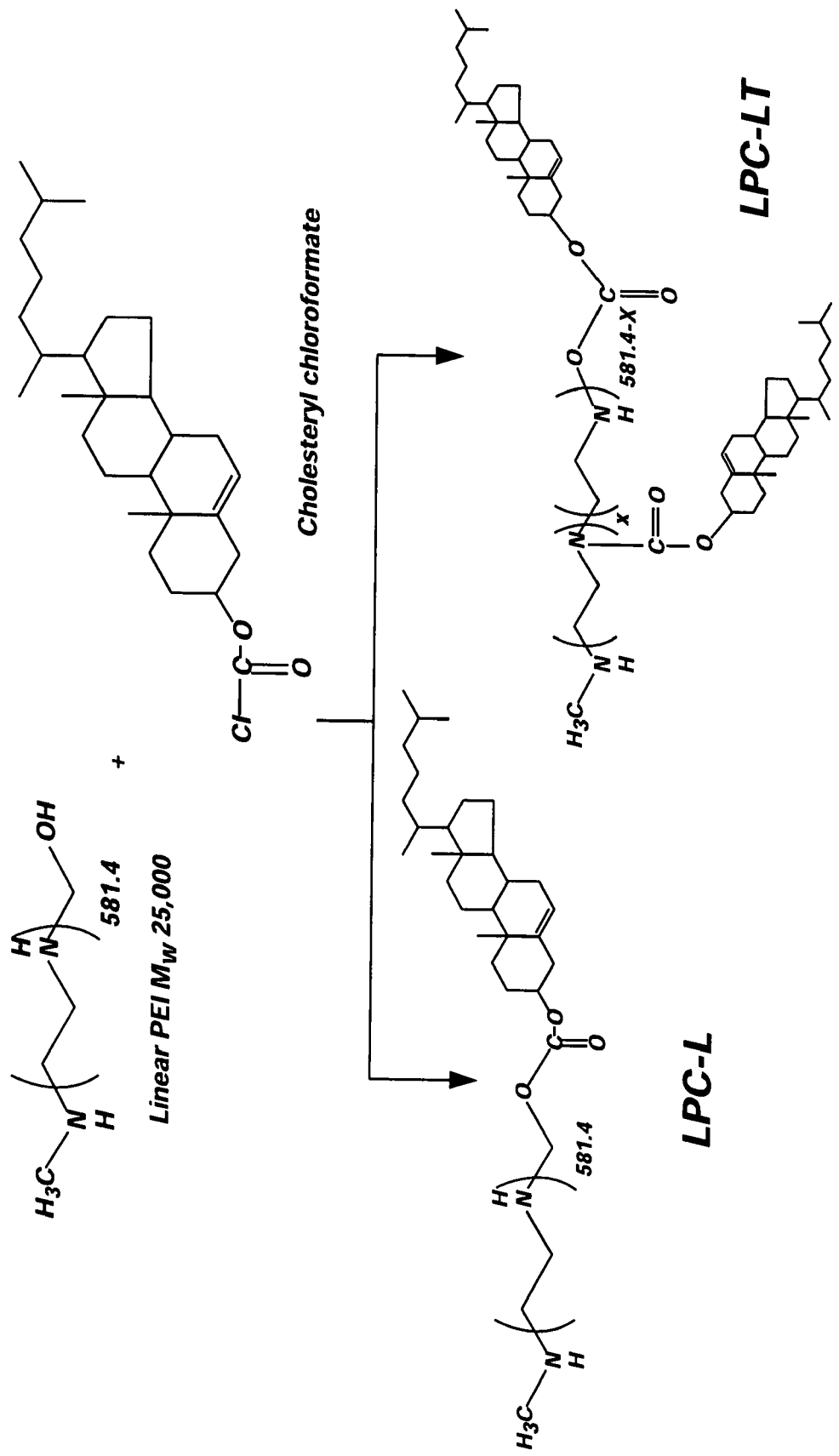
FIG. 1 shows a scheme for synthesis of linear polyethylenimine-cholesterol conjugates in linear-(L) and linear/T-shaped (LT) configurations.

Before the present compositions and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a cell" includes reference to two or more of such cells, reference to "an imine nitrogen atom" includes reference to two or more of such imine nitrogen atoms, and reference to "the sterol" includes reference to two or more of such sterols.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "LPC-L" means LPEI-cholesterol conjugates having a linear or "L" configuration (FIG. 1), wherein the cholesterol moiety is bound to the LPEI moiety through the terminal hydroxyl group of LPEI; "LPC-T" means LPEI-cholesterol conjugates having a T-shaped configuration (FIG. 3A), wherein the cholesterol moiety is bound to the LPEI moiety through a secondary amine nitrogen atom; and "LPC-LT" means LPEI-cholesterol conjugates having a combined linear- and T-shaped configuration (FIG. 1), wherein cholesterol moieties are bound to LPEI through both the terminal hydroxyl group and a secondary amine nitrogen atom. As used herein, "LPC conjugates" includes LPC-L, LPC-LT, and LPC-T. As used herein, "WSLP" means water-soluble lipopolymer, Affleck, D. G., Yu, L., Bull, D. A., Bailey, S. H., & Kim, S. W., Augmentation of myocardial transfection using TerplexDNA: a novel gene delivery system, 8 Gene Ther. 349-353 (2001); Lee, M., Rentz, J., Han, S. O., Bull, D. A., & Kim, S. W., Water-soluble lipopolymer as an efficient carrier for gene delivery to myocardium, 10 Gene Ther. 585-593 (2003). As used herein, "BPC" means BPEI-cholesterol conjugates.

The present invention relates to compositions for use as carriers for gene delivery. The present invention further relates to methods of making and methods of using these compositions. Certain aspects of the present invention include L-shaped, T-shaped, and LT-shaped linear polyethylenimine sterol conjugates. These conjugates are termed "L-shaped" when the sterol is conjugated to the terminal hydroxyl group of polyethylenimine such that the conjugate is linear. These conjugates are termed "T-shaped" when the sterol is conjugated to one or more secondary amine nitrogen atoms of polyethylenimine. These conjugates are termed "LT-shaped" when a sterol is conjugated to the terminal hydroxyl group and a sterol is conjugated to one or more secondary amine nitrogen atoms of polyethylenimine.

Linear polyethylenimine, or unbranched polyethylenimine, is commercially available.

Sterols that can be conjugated to linear polyethylenimine include cholesterol, cholestanol, coprosterol, epicholestanol, epicholesterol, ergostanol, α-ergostenol, β-ergostenol, γ-ergostenol, ergosterol, 22,23-dihydroergosterol, stigmasterol, stigmastanol, (3β)-7-dehydrocholesterol, desmosterol, allocholesterol, 24-hydroxycholesterol, 25-hydroxycholesterol, campesterol, $\alpha_1$-sitosterol, β-sitosterol, γ-sitosterol, lumisterol, pyrocalciferol, isopyrocalciferol, azacosterol, neoergosterol, dehydroergosterol, and the like. Cholesterol is illustrative of these sterols. These sterols all contain a 3-ol group for linking to the polyethylenimine polymer.

L-shaped linear polyethylenimine sterol conjugates can be made by conjugating an activated derivative of the sterol with linear polyethylenimine such that the activated sterol derivative bonds to the terminal hydroxyl group of linear polyethylenimine. For example, cholesterol can be activated by reacting cholesterol with an acid chloride, such as chloroformate, to result in cholesteryl chloroformate. This activated derivative is then reacted with linear polyethylenimine to result in the L-shaped linear polyethylenimine cholesterol conjugate. It will be appreciated that this method of synthesis results in a linker, in this example —O—CO—, being inserted between the sterol and the linear polyethylenimine.

LT-shaped linear polyethylenimine sterol conjugates can be made in a manner similar to that of the L-shaped conjugates, except that excess activated sterol derivative is permitted to react with the linear polyethylenimine. After the terminal hydroxyl groups have reacted with the activated sterol derivatives and formed bonds therewith, additional bonding reactions take place with secondary amine nitrogen atoms of the polyethylenimine polymer. When using cholesteryl chloroformate as the activated sterol for reaction with LPEI to form LT-shaped linear polyethylenimine sterol conjugates, a —O—CO— linker is formed upon bonding to the terminal hydroxyl group, and a —CO— linker is formed upon bonding to the secondary amine nitrogen atom.

T-shaped linear polyethylenimine sterol conjugates can be made by protecting the terminal hydroxyl group of linear polyethylenimine, bonding an activated sterol derivative to one or more secondary amine nitrogen atoms of the linear polyethylenimine polymer, and then deprotecting the terminal hydroxyl group. For example, linear polyethylenimine can be protected by reacting it with a protecting reagent, such as chlorotrimethylsilane, to result in the protected polymer. This intermediate can then be reacted with an activated sterol derivative, such as cholesteryl chloroformate. A —CO— linker is formed upon bonding to the secondary amine nitrogen atom. The resulting T-shaped, protected conjugate can then be deprotected by reacting it with a deprotecting reagent, such as trifluoroacetic acid, for removing the protecting group and resulting in the T-shaped linear polyethylenimine sterol conjugate as a final product.

Illustrative methods of activating the sterols are disclosed, but other methods known in the art can also be used. Such methods are limited only by functionality. Similarly, methods of protecting and deprotecting the terminal hydroxyl group of polyethylenimine are disclosed, but other methods known in the art are also considered within the scope of the invention. Such methods are also limited only by functionality.

Complexes of a nucleic acid to be delivered into a cell and the L-shaped, T-shaped, or LT-shaped linear polyethylenimine sterol conjugates, or mixtures thereof are made by mixing the nucleic acid with the selected conjugate or conjugates in appropriate ratios. Such ratios are limited only by functionality, however, N/P ratios of 1/1 to 30/1 are illustrative, and N/P ratios of 5/1 to 10/1 are typical.

In vitro transfection of mammalian cells is carried out according to standard transfection methodologies. Briefly, the cells are contacted with complexes containing the selected nucleic acid and conjugate, and the cells and complexes are permitted to incubate together for a selected period of time, usually several hours. The cell growth medium is then replaced, thus washing away most of the complexes that had not entered the cells. The cells are then incubated under conditions suitable for growth of the cells. Transfection efficiency can be determined, if desired, in a number of ways, such as assaying for the presence of the nucleic acid inside the cells or assaying for the expression of a product coded for by the nucleic acid, such as protein, inside the cells.

The following examples illustrate various aspects of the present invention and are not to be construed as limiting the scope of the invention.

Example 1

Synthesis of LPC-L

Figure 2:
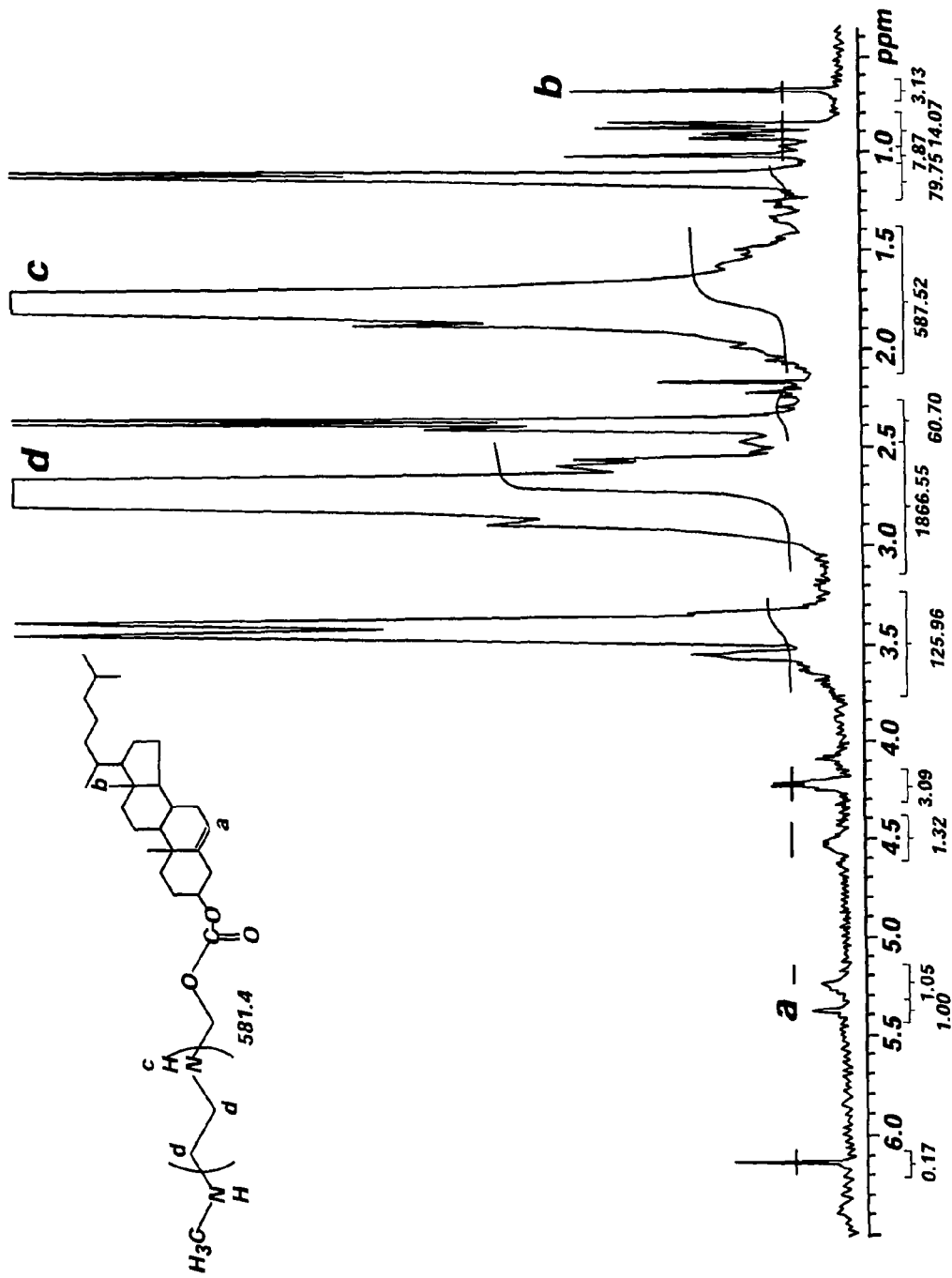
FIG. 2 shows a $^1$H NMR spectrum of LPC-L.

FIG. 1 shows a scheme for synthesis of LPC-L. LPEI (MW 25,000; 1.0 g=0.04 mmol; Polysciences, Warrington, Pa.) was dissolved in 150 mL of anhydrous methylene chloride (Sigma Chemical Co., St. Louis, Mo.) with heating in a hot water bath for about 20 minutes. The solution was then cooled and additional methylene chloride was added to return the volume to 150 mL. Next, about 0.018 g (0.04 mmol) of cholesteryl chloroformate (Aldrich Chemical Co., Inc., Milwaukee, Wis.) was dissolved in 3 mL of anhydrous methylene chloride and then added to the LPEI solution dropwise over about 10 minutes. The mixture was stirred over night, the solvent was removed by rotary evaporation, and the product was purified by solvent precipitation in acetone (Sigma Chemical), ethyl acetate (Sigma Chemical), and excess methylene chloride. The conjugate was dried and lyophilized prior to analysis by $^1$H NMR (Varian Mercury 400, Inc., Palo Alto, Calif.) and stored at −20° C. FIG. 2 shows a $^1$H NMR spectrum for LPC-L. The proton adjacent to the carbon-carbon double bond is indicated at a. The protons of the methyl group attached to carbon 13 of the steroid are indicated at b. The protons attached to nitrogen and carbon atoms of the polyethylenimine moiety are indicated at c and d, respectively.

Example 2

Synthesis of LPC-LT

FIG. 1 also shows a scheme for synthesis of LPC-LT. The procedure of Example 1 was followed except that an additional 0.036 g (0.08 mmol) of cholesteryl chloroformate was added to the solution after the first addition of cholesteryl chloroformate.

Example 3

Synthesis of LPC-T

Figure 3A:
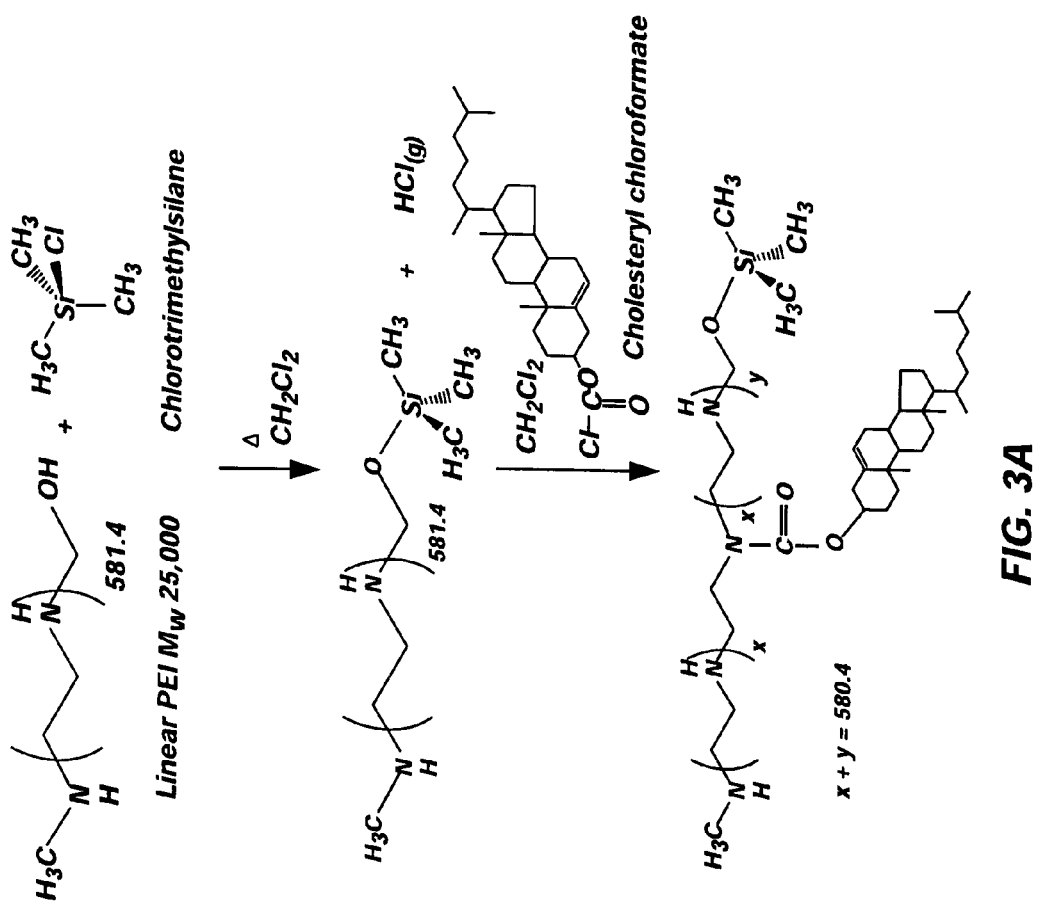
FIGS. 3A-B show a scheme for synthesis of linear polyethylenimine-cholesterol conjugates in a T-shaped (T) configuration.
Figure 3B:
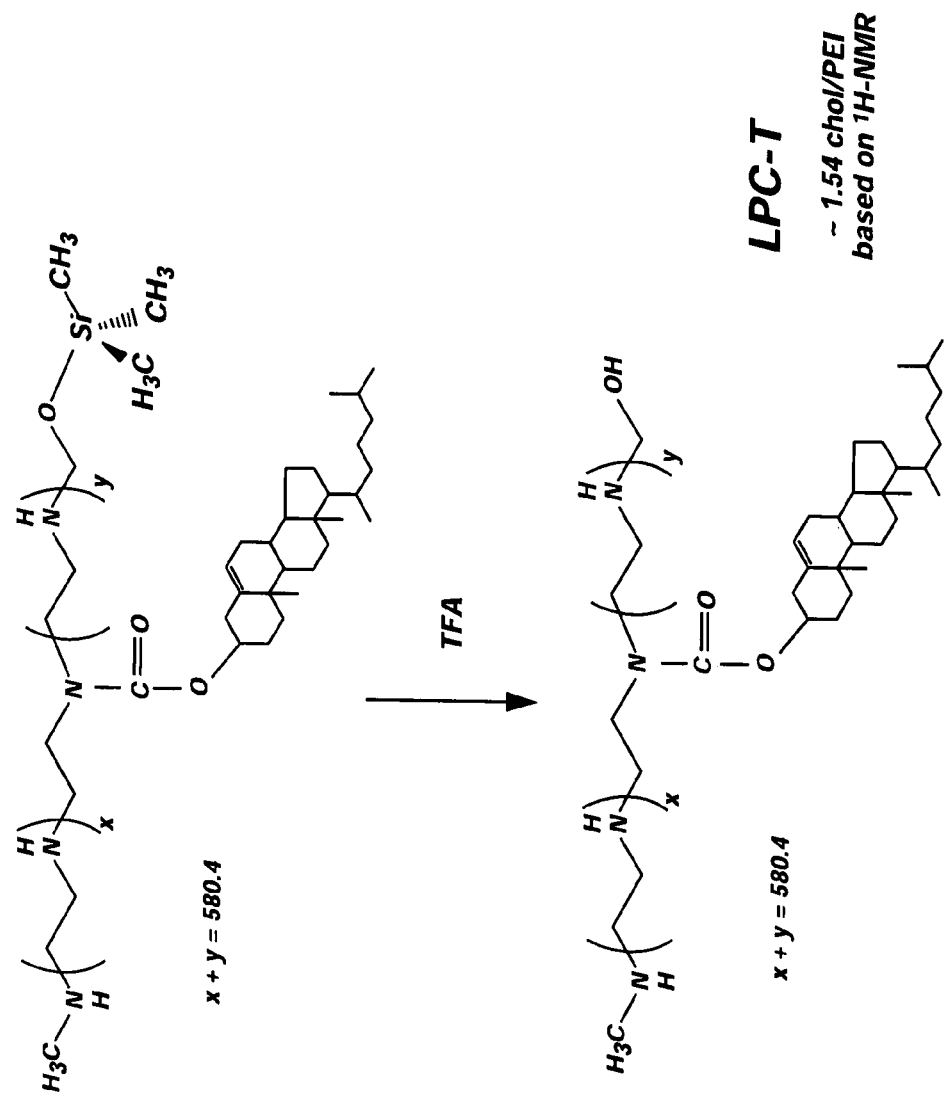

FIGS. 3A-B show a scheme for synthesis of LPC-T. LPEI (MW 25,000; 1.0 g=0.04 mmol) was dissolved in 150 mL of anhydrous methylene chloride (Sigma Chemical Co., St. Louis, Mo.) with heating in a hot water bath for about 20 minutes. The clear solution was removed form the hot water bath, cooled, and then additional methylene chloride was added to return the volume to 150 mL. The solution was then stirred for 15 min. at room temperature, after which 200 μL of anhydrous triethylamine (TEA; Sigma Chemical) was added, and stirring was continued for 5 min. To protect the terminal hydroxyl group, 60 μL (0.06 mmol) of 1 M chlorotrimethyl silane (Aldrich Chemical) was added, forming an HCl$_{(g)}$ cloud over the solution. The mixture was stirred overnight.

Next, 36 ml (0.08 mmol) of cholesteryl chloroformate was dissolved in 3 mL of anhydrous methylene chloride and added dropwise to the trimethylsilane (TMS)-protected LPEI over 10 min. Then, the cholesterol was conjugated to the secondary amine on the LPEI by a carbamate bond. The reaction was stirred overnight. Deprotection of the LPC-T-TMS was completed by adding 3 mL of trifluoroacetic acid (TFA; Sigma Chemical), which caused the LPC-T to precipitate. The sample was dried on a rotary evaporator, dissolved in 20 mL of ultrapure water, and purified by dialysis (MWCO 6,000 to 8,000) for three days. The conjugate was lyophilized and analyzed by $^1$H NMR and stored at −20° C.

Example 4

Amplification and Purification of pORF-mIL-12elasti

Interleukin-12 (IL-12) is a heterodimeric cytokine composed of p35 and p40 chains. The p35 chain is also called the IL-12 alpha, cytotoxic lymphomaturation factor 35 kD subunit (CLMFp35), or NK cell stimulatory factor chain 1 (NKSF1). The p40 chain is also called the IL-12 beta, cytotoxic lymphomaturation factor 40 kD subunit (CLMFp40), or NK cell stimulatory factor chain 2 (NKSF2). IL-12 is a multifunctional cytokine secreted by a variety of cells including macrophages and B cells.

IL-12 has emerged as one of the most efficient antitumor cytokines. To avoid systemic toxicity of systemic delivery of the recombinant protein, gene transfer of IL-12 has been performed and has shown to be efficient at reducing tumor growth. Numerous studies have reported regression and even complete eradication of established primary tumors, as well as reduction of metastases in different tumor models. S. Hiscox & W. G. Jiang, Interleukin-12, an emerging anti-tumour cytokine, 11 In Vivo 125-132 (1997).

IL-12 antitumor activity is due to its ability to elicit Th1 responses. In most cases, CTL and NK immune responses were elicited and accounted for the immediate tumor regression. Importantly also, IL-12 expression at the tumor site generated a long term protective antitumor immune response. IL-12 antitumoral properties are also due to its direct ability to inhibit angiogenesis. IL-12 gene transfer is now being tested in clinical trials. Y. Sun et al., Vaccination with IL-12 gene-modified autologous melanoma cells: preclinical results and first clinical phase I study, 5 Gene Ther. 481-490 (1998).

Plasmids encoding IL-12 are commercially available (InvivoGen, San Diego, Calif.). Since the expression of IL-12 requires coordinated expression of both the p35 and p40 subunits, researchers have constructed plasmids coding for both subunits using a linker. R. Anderson et al., Construction and biological characterization of an interleukin-12 fusion protein (Flexi-12): delivery to acute myeloid leukemic blasts using adeno-associated virus, 8 Hum. Gene Ther. 1125 (1997); Y. L. Lee et al., Construction of vectors expressing bioactive heterodimeric and single-chain murine interleukin-12 for gene therapy, 9 Hum. Gene Ther. 457 (1998). Advantages of expressing IL-12 as a single polypeptide versus a promoter for each coding sequence or an internal ribosome entry site (IRES) include the expression of equal amounts of each subunit, preventing the production of free p40, which antagonizes IL-12 activity, and allowing a more compact construct. The p35 and p40 subunits are linked by two bovine elastin motifs (10 amino acid residues). The bovine elastin linker has the advantages of resisting proteases, lacking secondary structure due to the presence of "destructuring amino acids" such as proline and glycine, and providing an extended and flexible structure, which allows both of the IL-12 subunits to fold and interact properly. In its murine form, the IL-12 expression plasmid contains the p40 subunit-coding portion 5' to the p35-subunit-coding portion.

The pORF-mIL-12elasti vector (InvivoGen, San Diego, Calif.) contains the mouse p35 and p40 subunits of IL-12 linked by a linker comprising two bovine elastin motifs and driven by a human T-cell leukemia virus (HTLV) promoter. Plasmids were amplified using JM109 competent cells and were purified using the Qiagen Endofree Maxi Plasmid Purification Kit (Qiagen, Valencia, Calif.) according to the manufacturer's protocol. UV spectrophotometry at 260/280 nm and gel electrophoresis were carried out for determining the concentration, integrity, and purity of the amplified plasmid. Purity ($A_{260}/A_{280}$) was greater than 1.8, and appropriate bands were seen upon restriction enzyme analysis.

Example 5

Preparation of LPC/pORF-mIL-12elasti Complexes

LPC conjugates and BPEI were concentrated at 1.5 mg/mL in ultrapure water and were stored at 4° C. Turbidity was seen with the LPC-L and LPC-LT, most likely due to intermolecular hydrogen bond formation. No visual turbidity was seen with LPC-T. The LPC conjugate-containing solutions were heated in a hot water bath at about 55° C. for 15 minutes to break the intra- and inter-molecular hydrogen bonds of the conjugates. After cooling to room temperature, both the LPC conjugate solutions and pORF-mIL-12elasti plasmid DNA were separately diluted to a final concentration of 5% glucose at 100 µL each at a pDNA concentration of 0.1 mg/mL. The LPC conjugate solution was added to the pORF-mIL-12elasti solution and thoroughly mixed. Complex formation was allowed for 15 min. at ambient conditions. Aggregation of LPC-LT/pORF-mIL-12elasti complexes was seen after 30 min.

Example 6

Gel Retardation Assay

Figure 4:
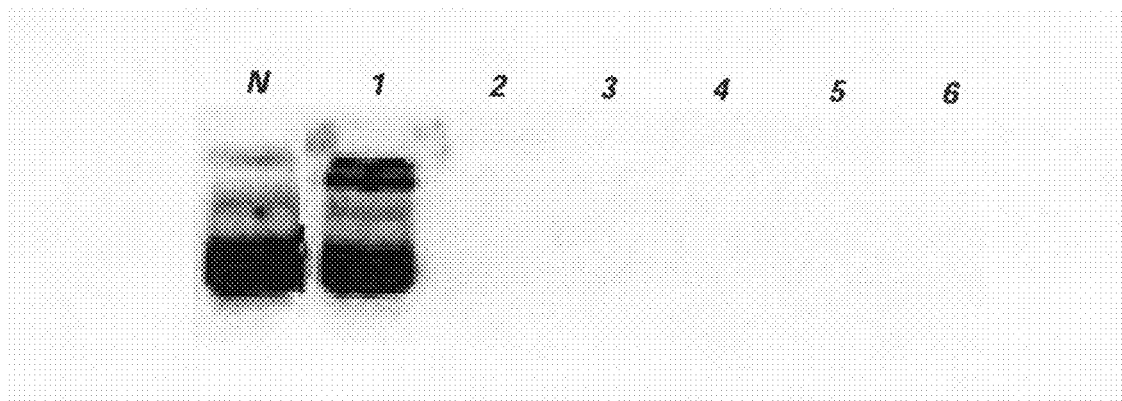
FIG. 4 shows a gel retardation assay: N—naked plasmid DNA, 1—N/P 1/1, 2—N/P 5/1, 3—N/P 10/1, 4—N/P 15/1, 5—N/P 20/1, 6—N/P 30/1.

Plasmid DNA condensation by the LPC conjugates, prepared according to the procedure of Example 5, was evaluated by a gel retardation assay. The LPC conjugate/pORF-mIL12elasti complexes were electrophoresed on a 1% agarose gel pretreated with 0.5 mg/mL ethidium bromide in 1×Tris-base-acetate-EDTA (TAE) buffer at 84 V. Naked pORF-mIL-12elasti DNA was used for the marker lane. FIG. 4 shows that retardation of mobility of the plasmid DNA occurred at an N/P ratio of 1/1 and higher, as compared to mobility of the naked plasmid DNA. This indicates that the plasmid DNA was complexed with the LPC-L carrier.

Example 7

DNase Protection Assay

LPC conjugate/pORF-mIL-12elasti complexes were prepared at N/P ratios of 5/1, 10/1, 20/1, and 30/1 at a final pDNA concentration of 0.1 mg/mL and 500 mL total volume. The samples were incubated at ambient conditions for 20 min. Then, 50 µL of stop solution (200 mM NaCl, 20 mM EDTA, and 1% SDS) was added to eight PCR tubes for each LPC conjugate/pDNA sample, representing the appropriate DNase stop time of 0, 2, 5, 15, 30, 60, and 180 min. Next, 50 µL of each LPC conjugate/pDNA complex was removed and added to the 0 min incubation tube and gently mixed. To the remaining LPC conjugate/pDNA complexes, 50 µL of RQ1 RNase-free DNase (Promega, Madison, Wis.) was added, gently mixed, and incubated at 37° C. At the appropriate stop times, 50 µL of each sample was removed and added to the stop solution tube. To dissociate the pDNA from the LPC conjugates, the samples were incubated, followed by ethanol precipitation. The pellets were redissolved in 10 µL of molecular biology grade water and analyzed by 1% agarose gel electrophoresis.

Figure 5:
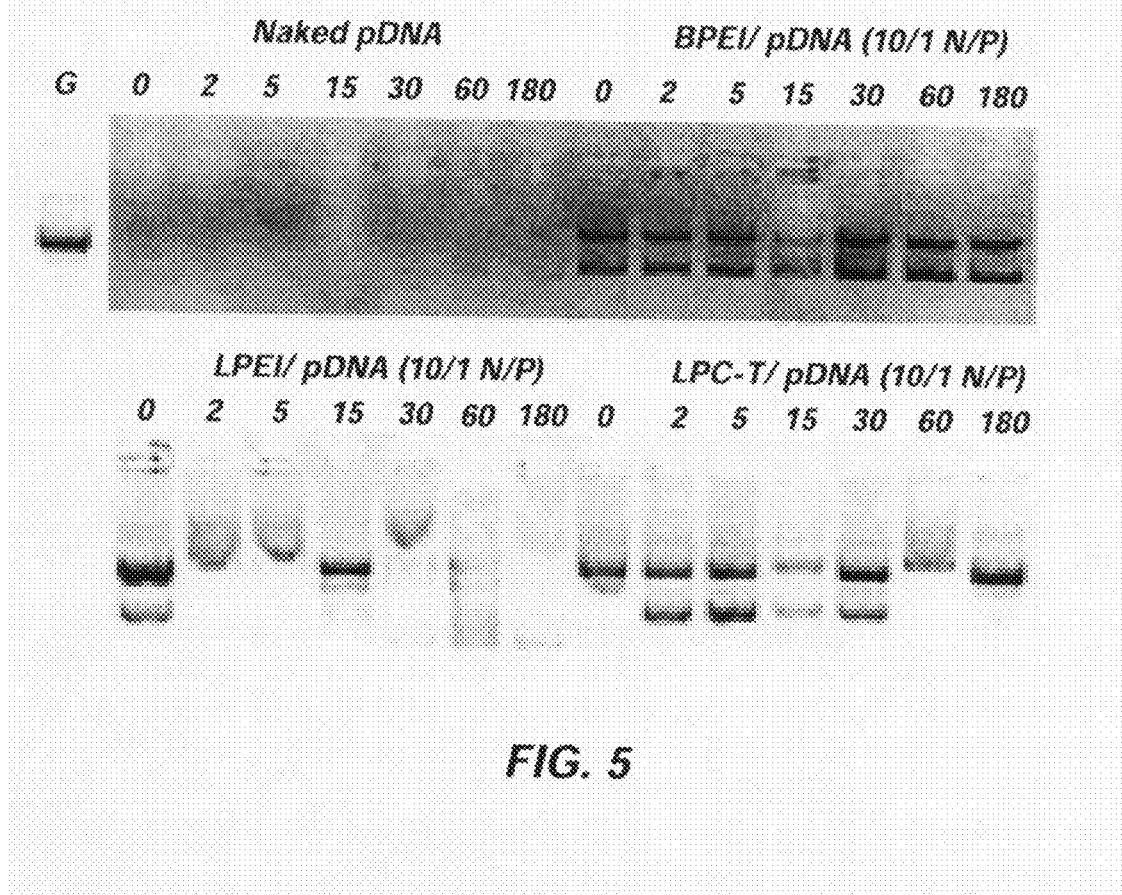
FIG. 5 shows a DNase protection assay: C—control plasmid DNA not exposed to DNase; naked pDNA—plasmid DNA exposed to DNase, but not complexed with BPEI, LPEI, or LPC-T; BPEI/pDNA—plasmid DNA exposed to DNase and complexed with BPEI, N/P 10/1; LPEI/pDNA—plasmid DNA exposed to DNase and complexed with LPEI, N/P 10/1; LPC-T/pDNA—plasmid DNA exposed to DNase and complexed with LPC-T, N/P 10/1.

FIG. 5 shows the results of LPC-T/pDNA (N/P 10/1) complexes in protecting from digestion by DNase as compared to naked pDNA, BPEI/pDNA (N/P 10/1), and LPEI/pDNA (N/P 10/1). The LPC-T carrier protected the pDNA from DNase digestion about as well as BPEI and better than LPEI.

Example 8

Particle Size and Zeta Potential

LPC conjugate/pDNA complexes were measured at several N/P ratios for particle size and zeta potential on a Brookhaven Instruments Corp. (Holtsville, N.Y.) ZetaPALS. Experimental conditions were 37° C. using a 677 nm wavelength at a constant angle of 15°. Smoluchowski's formula was used to calculate the zeta potential from the electrophoretic mobility. Values for the particle size are effective mean diameters.

Figure 6:
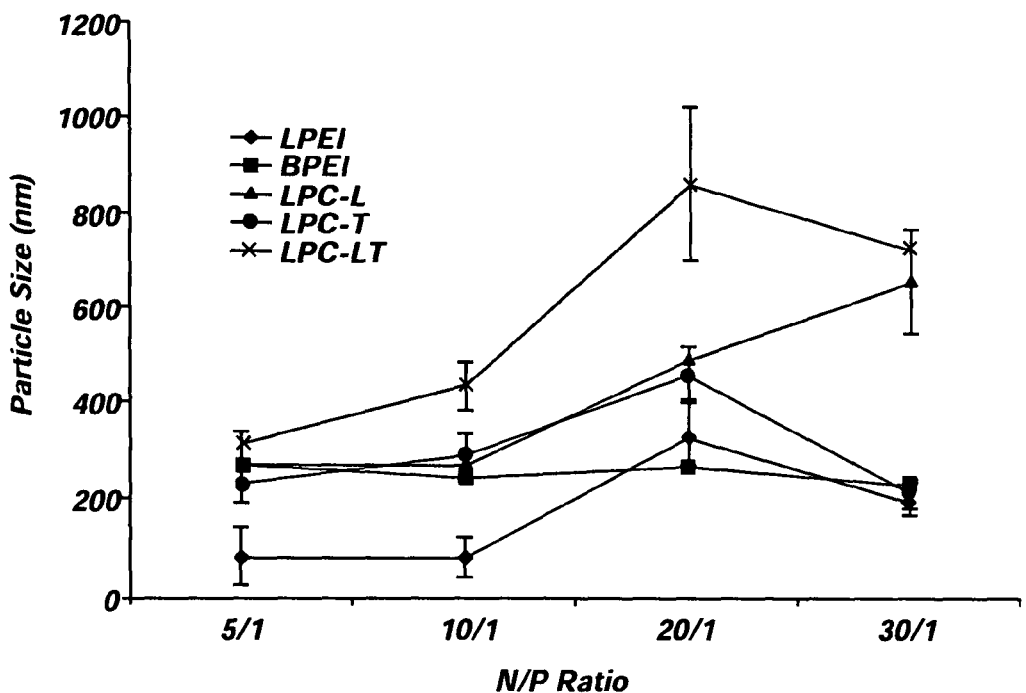
FIG. 6 shows particle sizes of DNA-containing complexes comprising LPEI (◆), BPEI (■), LPC-L (▲), LPC-T (●), and LPC-LT (X) at N/P ratios from 5/1 to 30/1, as determined with a zeta potential analyzer.
Figure 7:
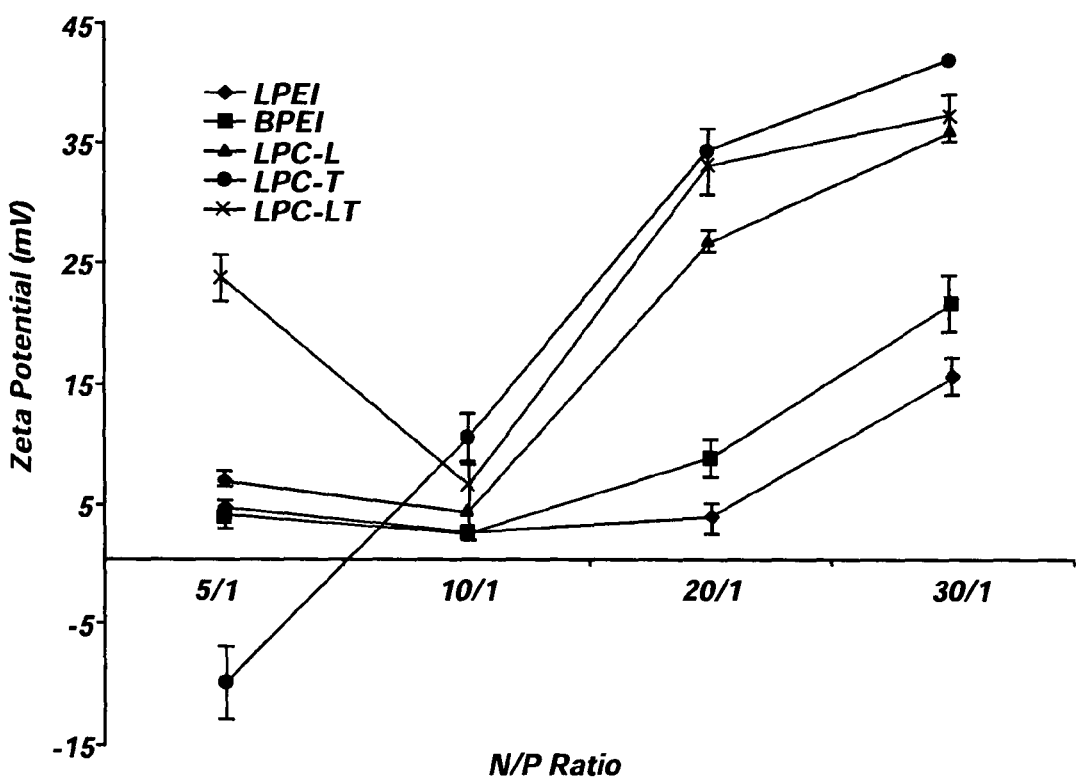
FIG. 7 shows zeta potentials of DNA-containing complexes comprising LPEI (◆), BPEI (■), LPC-L (▲), LPC-T (●), and LPC-LT (X) at N/P ratios from 5/1 to 30/1.
Figure 8:
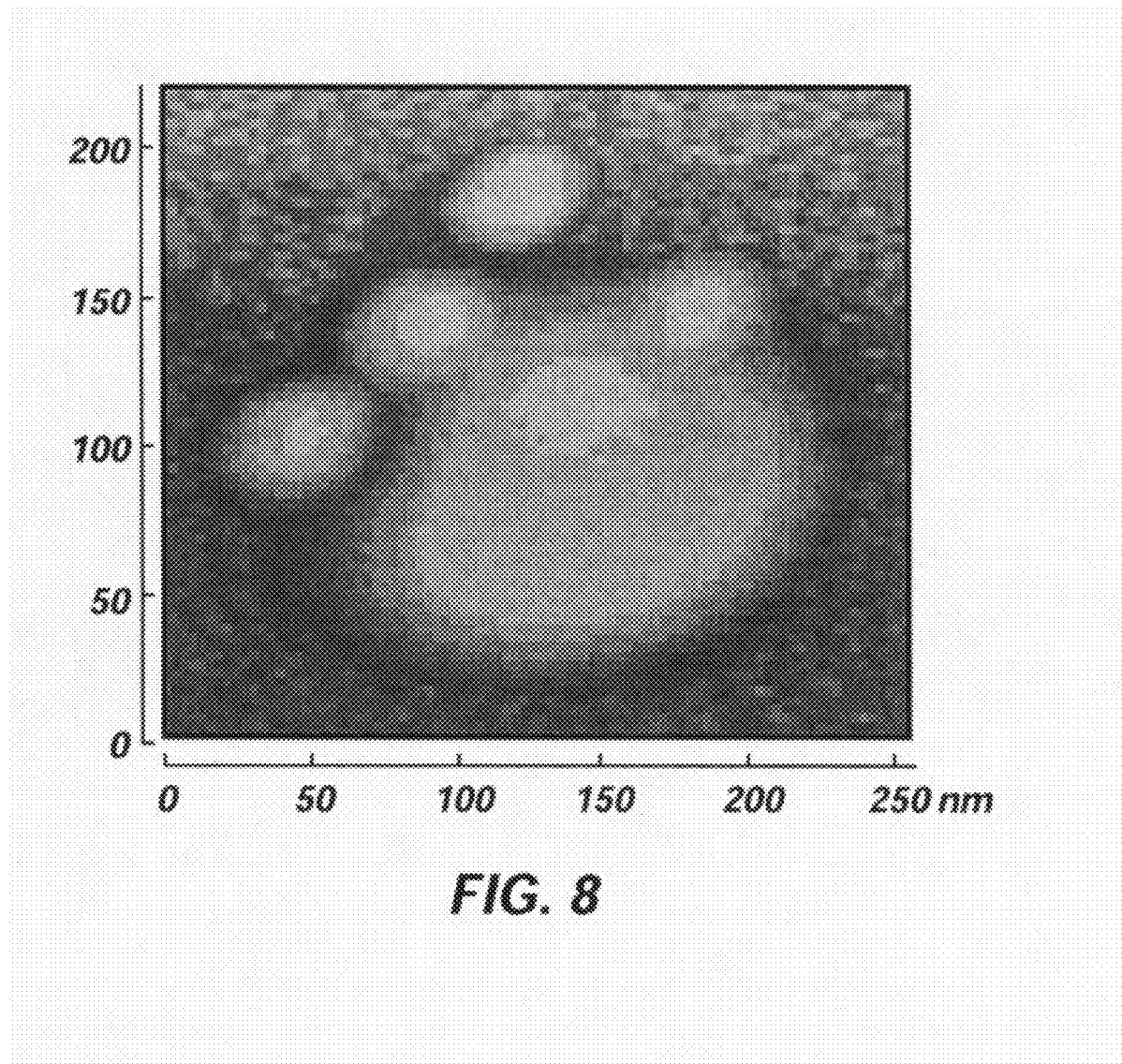
FIG. 8 shows an atomic force microscopy (AFM) image of LPC-T/pORF-mIL-12elasti, N/P 10/1.

FIGS. 6 and 7 show the particle sizes and zeta potentials, respectively, of complexes containing LPEI, BPEI, LPC-L, LPC-T, and LPC-LT. The mean particle size for LPC-T/pDNA complexes remained relatively constant over the range of N/P 5/1 to 30/1, with a mean diameter of about 275 nm (FIG. 6). A dramatic particle size change was observed for the LPEI, LPC-L, and LPC-LT complexes from N/P 10/1 to 20/1. The LPC-LT complexes showed a particle size inappropriate for us in vivo (>300 nm). The slopes of the particle size curves for LPC-LT, LPEI, and LPC-L from N/P 10/1 to 20/1 were quite similar; moreover, this trend was retained in the zeta potential measurements. LPC-T complexes were negatively charged at an N/P ratio of 5/1; however, the complexes quickly became cationic upon doubling the number of nitrogen residues to N/P 10/1 (FIG. 8).

Example 9

Atomic Force Microscopy

Surface morphology was determined by AFM according to the procedure of D. Y. Furgeson et al., supra. Briefly, 9.9 mm mica disks were soaked in 33 mM magnesium acetate for a minimum of 24 hr to promote stronger pDNA binding by the divalent magnesium ions rather than the monovalent potassium ions. The mica was sonicated for 30 min in ultrapure water and subjected to glow discharge for 15 s in a vacuum between 100-200 mTorr. Upon exposure to air, 20 µL of 0.1 mg/mL LPC conjugate/pDNA was placed on the mica surface for 2 min, after which the mica was gently rinsed with distilled water and slowly blown dry with nitrogen. Imaging was completed at room temperature using a Digital Instruments Nanoscope II SFM (Santa Barbara, Calif.) in tapping mode.

FIG. 8 shows an AFM image of LPC-T/pORF-mIL-12elasti, N/P 10/1. These results show the complex morphology to be roughly spherical with a discrete particle size of about 250 nm at 30 and 60 min. However, at 90 min postmixing, small satellites were seen to be merging with the about 250 nm LPC-T complex. The particle size for LPC-T/pORFmIL-12elasti N/P 10/1 from dynamic light scattering (DLS) and AFM were both about 250 nm.

Example 10

In Vitro Transfection

B16-F0 murine melanoma, Renca murine renal cell carcinoma, and MCF7 human breast carcinoma cells were grown and maintained in Rosewell Park Memorial Institute (RPMI 1640) medium (Hyclone, Logan, Utah) supplemented with 10% fetal bovine serum (FBS, Hyclone), 100 U/mL penicillin, 100 U/mL streptomycin, and 50 µg/mL gentamicin at 37° C. and humidified 5% $CO_2$.

About 5,000 cells (B16-F0 or Renca) were seeded on 96-well plates in RPMI 1640 medium containing 10% FBS and antibiotics. The plates were incubated at 37° C. and humidified 5% $CO_2$ until cell confluency reached about 70%. At this point, cells were transfected with LPC conjugate/pORF-mIL-12elasti prepared at various N/P ratios ranging from 1/1 to 30/1. Then, 0.1 µg of pORF-mIL-12elasti was loaded per 100 µL of medium (RPMI 1640+10% FBS). Cells were incubated for 4 hr in the presence of complexes and 10% FBS at standard incubator conditions. After 4 hr, the cell medium was replaced with 100 µL of fresh RPMI 1640+10% FBS, and the cells were further incubated for an additional 20 hr under the same conditions, resulting in a total transfection time of 24 hr. The cell medium was removed for ELISA, since mIL-12 p70 is a secreted protein. Untreated cells in addition to cells treated with naked pDNA alone were used as controls.

Levels of mIL-12 p70 were measured with a BDOptEIA™ ELISA set for mIL-12 p70 (Pharmingen, San Diego, Calif.) as per the manufacturer's instructions. Levels of mIL-12 p70 were reported as pg/mL.

Figure 9:
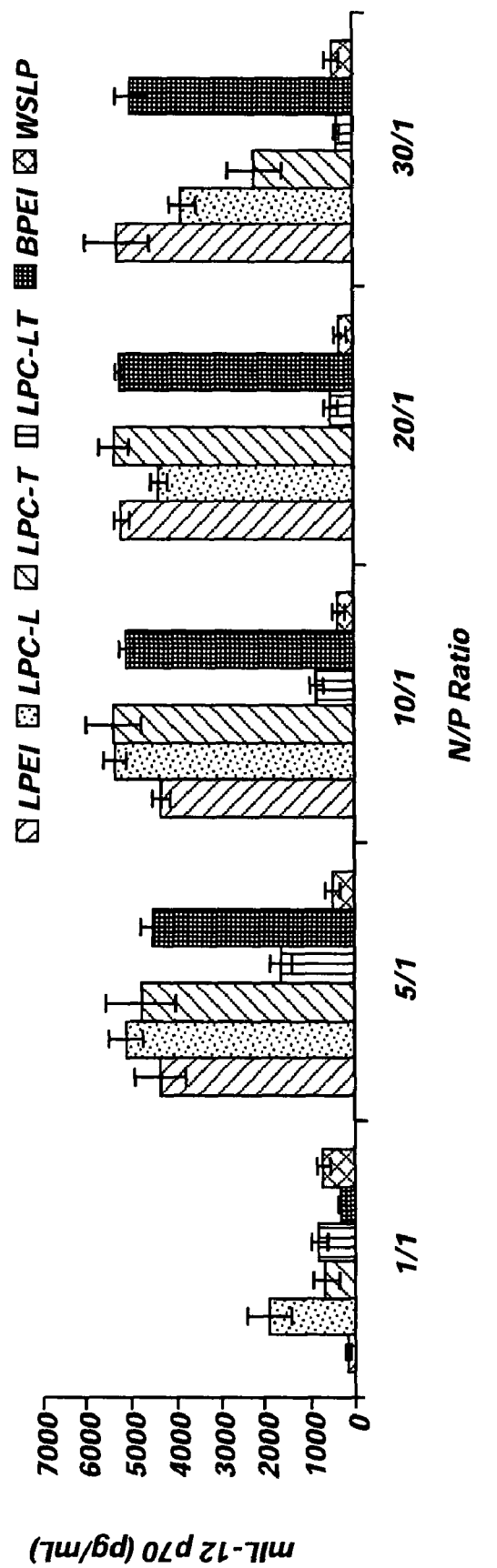
FIG. 9 shows the results of transfection assays in B16-F0 murine melanoma cells with 0.1 µg of pORF-mIL-12elasti and LPEI, LPC-L, LPC-T, LPC-LT, BPEI, or WSLP at N/P ratios from 1/1 to 30/1; naked pDNA control yielded 230±80 pg/mL, and BPEI and BPC provided the same levels of protein expression; data reported as mean±σ, n=8.

FIG. 9 shows the results of transfection assays with LPEI, LPC-L, LPC-T, LPC-LT, BPEI, and WSLP at N/P ratios from 1/1 to 30/1. At the optimal N/P ratios of 5/1 and 10/1, LPC-L and LPC-T provided higher transfection levels than BPEI, BPC, and LPEI of the same molecular weight. At an N/P ratio of 5/1, LPC-L resulted in greater than 13% more transfected cells than BPEI and greater than 18% more transfected cells than LPEI. Similarly, LPC-T resulted in greater than 5% more transfected cells than BPEI and greater than 10% more transfected cells than LPEI. At an N/P ratio of 10/1, LPC-L resulted in greater than 6% more transfected cells than BPEI and greater than 23% more transfected cells than LPEI. Similarly, LPC-T resulted in greater than 6% more transfected cells than BPEI and greater than 23% more transfected cells than LPEI.

Example 11

Cell Viability

A Cell Counting Kit-8 (CCK-8) (Dojindo Molecular Technologies, Inc., Gaithersburg, Md.) was used to evaluate the cytotoxicity of the LPC conjugates. About 5,000 cells (B16-F0 or Renca) were seeded on a 96-well plate with RPMI+10% FBS and incubated at 37° C. and humidified 5% $CO_2$ until confluency reached about 70%. LPC conjugate/pDNA complexes were prepared at various N/P ratios ranging from 1/1 to 30/1. Cells were transfected with 0.1 µg pORF-mIL-12elasti in the presence of 10% FBS for 4 hr, after which the medium was changed and transfections proceeded for an additional 20 hr in the presence of 10% FBS. After removal of the surrounding medium containing the excreted mIL-12 p70, 10 mL of thawed CCK-8 solution was added to each well. Plates were incubated for 1 to 1.5 hr at the same incubator conditions, after which the absorbance was read at 450 nm with a reference wavelength of 600 nm. Cell viability was calculated as $$\text{Cell viability (\%)} = (OD_{450(sample)}/OD_{450(control)}) \times 100,$$

where $OD_{450(sample)}$ is the absorbance at 450 nm of the transfected cells and $OD_{450(control)}$ is the absorbance at 450 nm of the negative control (non-transfected cells).

Figure 10:
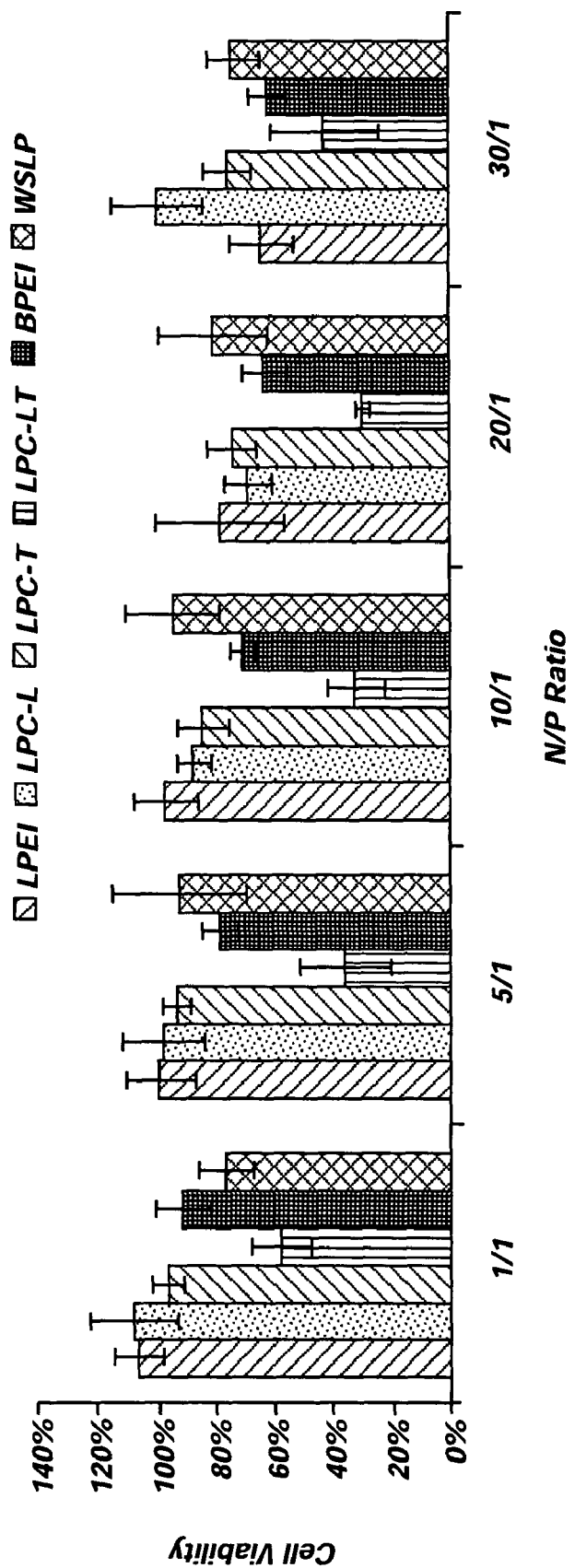
FIG. 10 shows the results of cell viability assays in B16-F0 murine melanoma cells with 0.1 µg of pORF-mIL-12elasti and LPEI, LPC-L, LPC-T, LPC-LT, BPEI, or WSLP at N/P ratios from 1/1 to 30/1; naked pDNA control yielded 95±8% cell viability; data reported as mean±σ, n=8.

FIG. 10 summarizes these results. At the optimal N/P ratios of 5/1 and 10/1, LPC-L and LPC-T were less cytotoxic than BPEI. At an N/P ratio of 5/1, LPC-L showed greater than 25% more cell viability than BPEI and about 2% lower cell viability than LPEI. Similarly, LPC-T exhibited greater than 19% more cell viability than BPEI and about 7% lower cell viability than LPEI. At an N/P ratio of 10/1, LPC-L exhibited greater than 24% more cell viability than BPEI and about 10% lower cell viability than LPEI. Similarly, LPC-T showed greater than 18% more cell viability than BPEI and about 15% lower cell viability than LPEI.

Example 12

In this example, 300,000 Renca or B16-F0 cells were seeded on six-well plates in RPMI 1640 medium supplemented with 10% FBS and antibiotics, according to the procedure of Example 10. The plates were incubated at 37° C. and humidified 5% $CO_2$ overnight. The following day the cells were transfected with 2 µg of pCMS-EGFP (Clontech Laboratories, Inc., Palo Alto, Calif.) in the presence of serum for 4 h, after which the medium was replaced with fresh RPMI 1640+10% FBS for an additional 44 h. Cells were trypsinized, centrifuged, and suspended in PBS prior to flow cytometry analysis.

Flow cytometric analysis of EGFP-labeled Renca and B16-F0 cells was carried out using a FACScan flow cytometer and analyzed with accompanying Cell Quest software (Becton Dickinson, Franklin Lakes, N.J.).

Table 1 shows that LPC-L/pEGFP consistently gave the highest levels of positively transfected cells in addition to the highest geometric mean of EGFP expression. For the Renca cells, the percentage of gated cells was nearly 2-times that of BPEI for LPC-T and LPEI. LPC-L levels were nearly 32-times that of BPEI; however, there is not a direct relationship between the percentage of cells gated and geometric mean of the fluorescence detected. Both BPEI and LPEI gave significantly higher percentages of B16-F0 cells that were positive for EGFP, but the geometric mean for LPC-L was more than 4-times that of BPEI. B16-F) cells transfected with LPC-T/pEGFP showed half the percentage of positive cells, but the geometric means were quite close.

TABLE 1

| Flow Cytometry of pEGFP Expression Following Transfection | | | | |
|---|---|---|---|---|
| | Renca | | B16-F0 | |
| | % Gated[a] | Geom. Mean[b] | % Gated | Geom. Mean |
| | C- | | | |
| average | 0.38 | 72.73 | 0.43 | 50.74 |
| SD | 0.18 | 4.03 | 0.27 | 6.03 |
| | Naked pDNA | | | |
| average | 0.42 | 69.57 | 0.45 | 48.69 |
| SD | 0.09 | 4.41 | 0.08 | 1.87 |

TABLE 1-continued

Flow Cytometry of pEGFP Expression Following Transfection

| | Renca | | B16-F0 | |
|---|---|---|---|---|
| | % Gated[a] | Geom. Mean[b] | % Gated | Geom. Mean |
| BPEI | | | | |
| average | 1.09 | 211.96 | 27.23 | 1552.44 |
| SD | 0.28 | 17.37 | 1.02 | 20.52 |
| LPEI | | | | |
| average | 2.08 | 549.12 | 10.14 | 1416.54 |
| SD | 0.23 | 77.70 | 0.27 | 58.43 |
| LPC-L | | | | |
| average | 32.14 | 2380.42 | 30.80 | 6484.99 |
| SD | 1.77 | 90.40 | 0.32 | 8347.57 |
| LPC-T | | | | |
| average | 2.23 | 804.26 | 13.47 | 1269.71 |
| SD | 0.12 | 130.63 | 0.06 | 49.18 |

[a]% Gated indicates the percentage of cells (per 10,000) that were positive for EGFP.
[b]Geom. Mean is indicative for the range of values from gated cells. Data reported as mean ± SD, n = 3.

Example 13

MCF-7 (human breast carcinoma) cells were used in an LDL-R study to determine whether receptor-mediated endocytosis of LPC-T/pDNA complexes was also possible. To calculate the concentration of anti-LDL-R antibody needed for saturation, 10,000 LDL-R sites per cell were assumed. Y. Li et al., Expression of alpha2-macroglobulin receptor/low-density lipoprotein receptor-related protein on surfaces of tumour cells: a study using flow cytometry, 111 Cancer Lett. 199-205 (1997). The concentration of anti-LDL-R antibodies was determined to be approximately 0.05 µM, assuming a fraction bound ($f_b$) of 0.99 and $K_A$ of $2 \times 10^9$. Five thousand MCF-7 cells were seeded onto a 96-well plate with 100 µL of RPMI 1640+10% FBS. Cells were incubated at standard conditions (Example 10) to about 70% confluency, after which a saturating concentration of the anti-LDL-R antibody (Oncogene Research Products, Boston, Mass.) was added in 100 µL of RPMI 1640+10% FBS containing LPC-T/pORF-mIL-12elasti. Cells were transfected with 0.1 µg of pORF-mIL-12elasti per 100 µL for 4 h, followed by replacing the wells with fresh medium and an additional 20 h for transfection. The pORF-mIL-12elasti vector was used to eliminate background levels of IL-12 p70.

Figure 11:
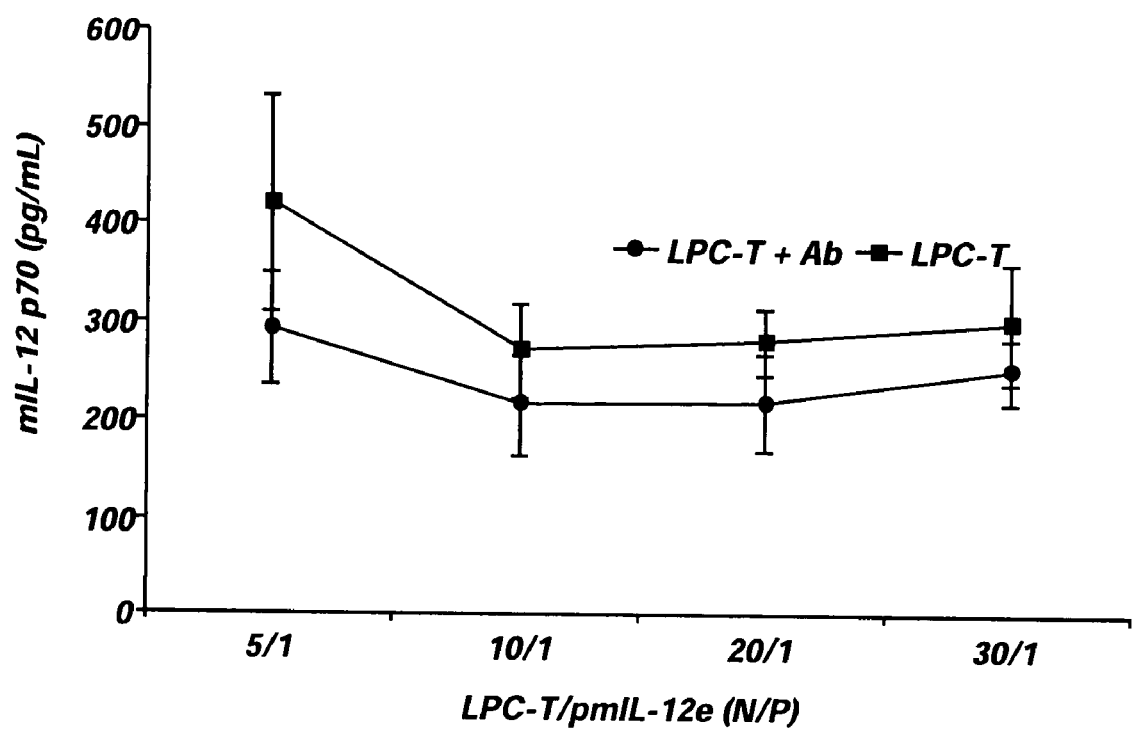
FIG. 11 shows the results of an anti-LDL-R antibody saturation study with MCF-7 cells transfected with LPC-T/pORF-mIL-12elasti (N/P 10/1); mIL-12 p70 ELISA data are reported as the mean±SD, n=8; LPC-T+antibody (●); LPC-T (■).

As shows in FIG. 11, mIL-12 p70 levels dropped by an average of about 20%, strongly indicating receptor-mediated endocytosis via the LDL-R pathway, in addition to the passive pathways of adsorptive endocytosis and pinocytosis. There was a sharp drop of mIL-12 p70 expression levels from N/P 5/1 to 10/1, however, levels remained relatively constant up to N/P 30/1 for the LPC-T and LPC-T plus LDL-R-antibody groups.

Example 14

Artificial pulmonary metastases were induced by intravenously injecting 100,000 Renca cells through the tail vein of 6-week, female BALB/c mice (Charles River Laboratories, Wilmington, Mass.) in 100 µl sterile PBS. Tumors were allowed to grow for 7 days with systemic (intravenous) injections beginning at day 8 with 20 µg of pORF-mIL-12elasti. Mice were injected weekly through the duration of the study (28 days) and weighed weekly to evaluate depression or cessation of normal eating habits and metabolic changes. One hundred thousand murine renal cell carcinoma (Renca) cells were subcutaneously injected into the right flank of 6-week, female BALB/c mice in 100 µl sterile PBS. Tumors were allowed to grow for 20 days with local (peritumoral) injections beginning at day 21 with 20 µg of PORF-mIL-12elasti. Therapeutic injections were given weekly and tumor size was determined by estimating the tumor volume based upon $0.5 \times a \times b^2$, where a is the length of the tumor along the long axis of the mouse, i.e. parallel to the spine and b is the length of the tumor in the perpendicular axis. Tumors were measured every three to four days.

To determine the organ distribution of both the polymer and plasmid DNA used in the therapeutic complexes, the plasmid DNA was labeled with ethidium monoazide bromide (EMA) (CAS #58880-05-0, phenanthridium, 3-amino-8-azido-5-ethyl-6-phenyl, bromide), which covalently binds and intercalates with the target plasmid. The maximum absorption for EMA is 464 nm while the emission maximum is 624 nm. This labeling procedure has been previously described, J. Zabner et al., Cellular and molecular barriers to gene transfer by a cationic lipid, 270 J. Biol. Chem. 18997-19007 (1995), but briefly, 1000 µg of pORF-mIL-12elasti (750 µL, 1.334 µg/µL) was mixed with 37.1 µg EMA (74.2 µL, 0.5 µg/µL) plus 1176.2 µL sterile water. The final molar ratio of nucleotide to probe was 34.3:1. This solution was incubated in the dark at room temperature for 10 min, after which it was exposed to UV light of principal wavelength 312 nm for 3 min. The resulting pORF-mIL-12elasti/EMA was purified with a NAP-25 column (Pharmingen) with sterile water as the running buffer. Finally, for increased stability of the EMA-labeled pDNA for in vivo biodistribution, the intercalated EMA was removed by adding cesium chloride to a final concentration of 1.1 g/mL and gently mixed until dissolved. At this point sodium citrate saturated isopropanol was added to the CsCl mixed pmIL-12e/EMA and mixed thoroughly. After allowing the sample to settle, two distinct phases were visible with the upper phase containing the free, unbound EMA, while the covalently linked EMA remained in the lower phase. The upper phase was discarded and the lower phase was washed with isopropanol followed by ethanol precipitation at −20° C. with 8 volumes of 1:3 TE/absolute ethanol. The resulting solution was centrifuged at 15,000×g for 10 min, the supernatant was discarded, and the pellet was redissolved in 300 µL sterile water. UV spectrophotometry determined the concentration and purity of the labeled pDNA at 260 nm and 280 nm.

The in vitro studies showed LPC-T to have high, intrinsic solubility, lower cytotoxicity profiles, and rates of transgene expression equal to or above that of BPEI of the same molecular weight. Consequently, for the in vivo biodistribution and efficacy studies, LPC-T was chosen as the carrier for the therapeutic plasmid, pmIL-12e. The labeling of LPC-T was accomplished by combining 100 mg LPC-T (3.93 µmol) with 5 mg BODIPY-FL SE (12.8 µmol) (CAS # 146616-66-24,4-difluoro-5,7-dimethyl-4-bora-3a,4a-diaza-s-indacene-3-propionic acid, succinimidyl ester) in DMSO. The solution was stirred overnight in the dark at room temperature. The labeled LPC-T was dialyzed against ultrapure water (MWCO 6,000-8,000) for 2 days in the dark, frozen, and lyophilized. The yield of LPC-T/BODIPY was ~23.1%, which is consistent with the typical loss of polymer bound to the dialysis membrane. The final LPC-T/BODIPY was dissolved in ultra-pure water at 1.25 mg/mL forming the stock solution. The maximum absorption and emission maximum for BODIPY-FL SE are 502 nm and 510 nm, respectively.

Following tail-vein injection of $10^5$ Renca cells to induce pulmonary metastases, fluorescently labeled LPC-T/BODIPY and pORF-mIL-12elasti/EMA were complexed at N/P 20/1 in a total volume of 200 µL. Although a lower N/P is desirable for in vivo applications, N/P 20/1 gave the highest differentiation between the Renca cell in vitro transfections, thus the N/P 20/1 was used in vivo. The target N/P ratio of 20/1 corresponds to a 2.57/1 weight/weight ratio. The polymer and pDNA solutions were mixed separately in 0.65 mL centrifuge tubes. Briefly, 41.2 µL of LPC-T/BODIPY (1.25 mg/mL), 25 µL glucose 20%, and 33.8 µL sterile water were combined for the polymer solution. Next, 6.1 µL of pORF-mIL-12elasti/EMA (3.282 mg/mL), 25 µL glucose 20%, and 68.9 µL sterile water were mixed together for the pDNA solution. The final volumes for both the polymer and pDNA solutions were 100 µL. The LPC-T/BODIPY solution was added to the pmIL-12e/EMA solution and thoroughly mixed and allowed to complex for 15 min in the dark resulting in 200 µL of an isotonic 5% glucose solution. These formulations remained constant throughout the study; however, the LPEI/pEGFP control group differed in its pDNA formulation: 5.85 µL pCMS-EGFP, 25 µL glucose 20%, and 69.15 µL sterile water.

After 15 min the numerous complexes were combined into one 1.7 mL centrifuge to allow for aspiration by the insulin syringe for injection. Then, 200 µL, corresponding to 20 µg pDNA, was aspirated and any air bubbles were removed. For systemic injections BALB/c mice were slowly injected through a distal tail vein site. If the injection was unsuccessful, then a more proximal tail vein site was used for the injections. In addition, the hood lights were not used for the biodistribution injections so as to limit any photobleaching possibilities. For the subcutaneous tumor model, local or peritumoral injections of 20 µg pDNA were administered. Upon inserting the needle tip below the tumor body, aspiration was carried out to confirm that a blood vessel had not been entered, after which the 200 µL was slowly injected. The significance between treatment groups and control groups was determined by statistical analysis using one-way ANOVA.

This LPC-T/pORF-mIL-12elasti study was to identify the biodistribution of both the polymer gene carrier and the plasmid cargo. Briefly, $10^5$ Renca cells were systemically injected and allowed to grow for 5 days. At this point pulmonary metastases have been shown to occur, although they are not visible to the naked eye. The biodistribution studies were designed to track both the polymer and pDNA for 3 days, thus the later time points were injected first since the tissue would not be harvested quickly. For the early time points, 200 µL of the 0.1 mg/mL pDNA complexes were injected with subsequent removal of the tissues of interest: heart, liver, lung, kidney, spleen, and blood. Mice were appropriately euthanized using a $CO_2$ chamber, following which the tissues were harvested. Blood was drawn and spun at 6500×g for 15 min to separate the serum from erythrocytes. Tissues were removed and stored in 24-well plates with PBS at 4° C.; however, serum samples were stored separately in 0.65 mL tubes. To read the fluorescent absorptions with the plate reader, the tissues were first homogenized with a Barnant Mixer Series 10 equipped with a Teflon plunger. Samples were appropriately diluted according to their tissue type and scaled against normal tissue background levels for these absorbances. All samples were normalized by their respective dilution factors and the results are shown in the FIGS. 12-13.

Figure 12:
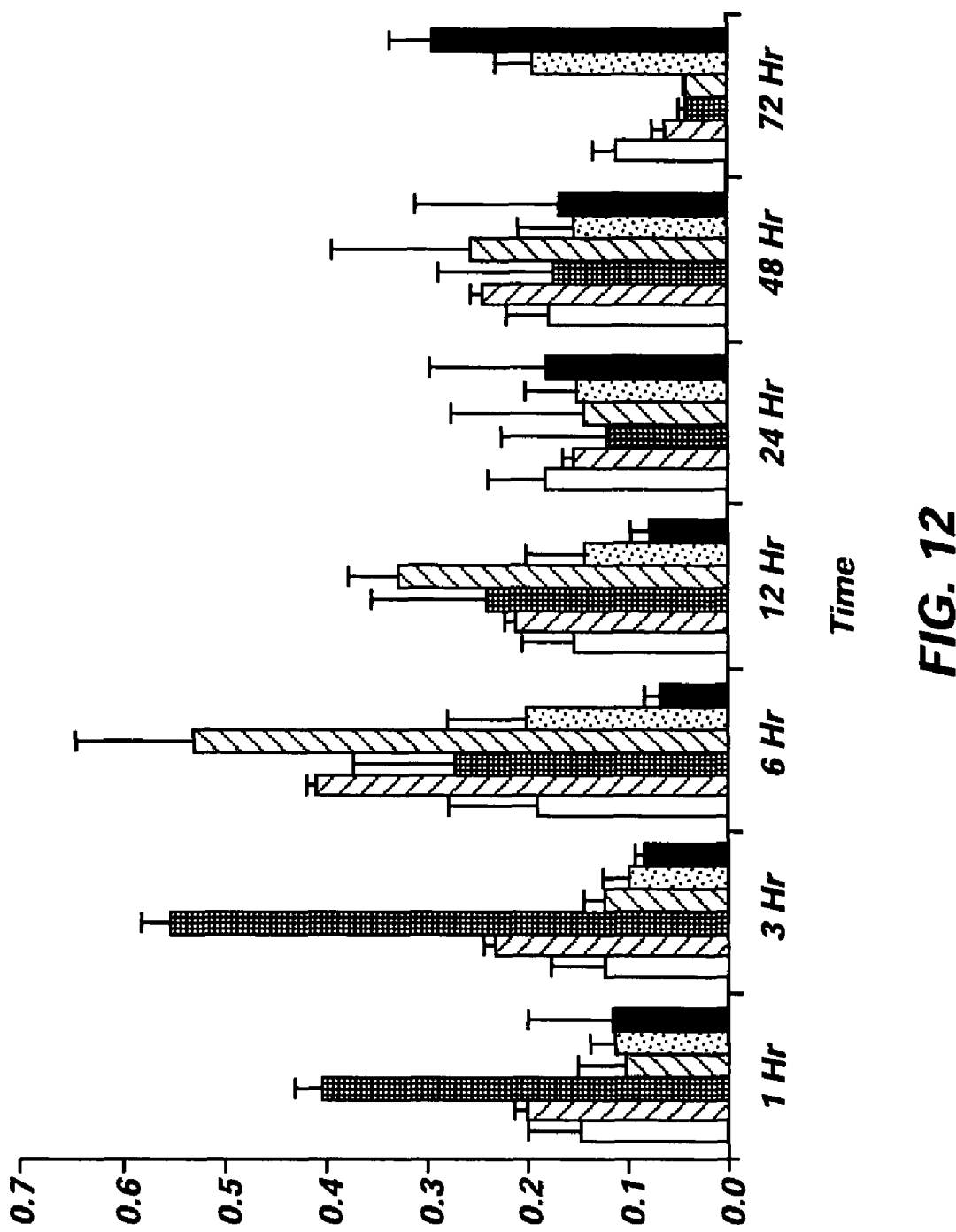
FIG. 12 shows in vivo biodistribution of LPC-T/BODIPY following systemic injection; data reported as mean±SD, n=5.
Figure 13:
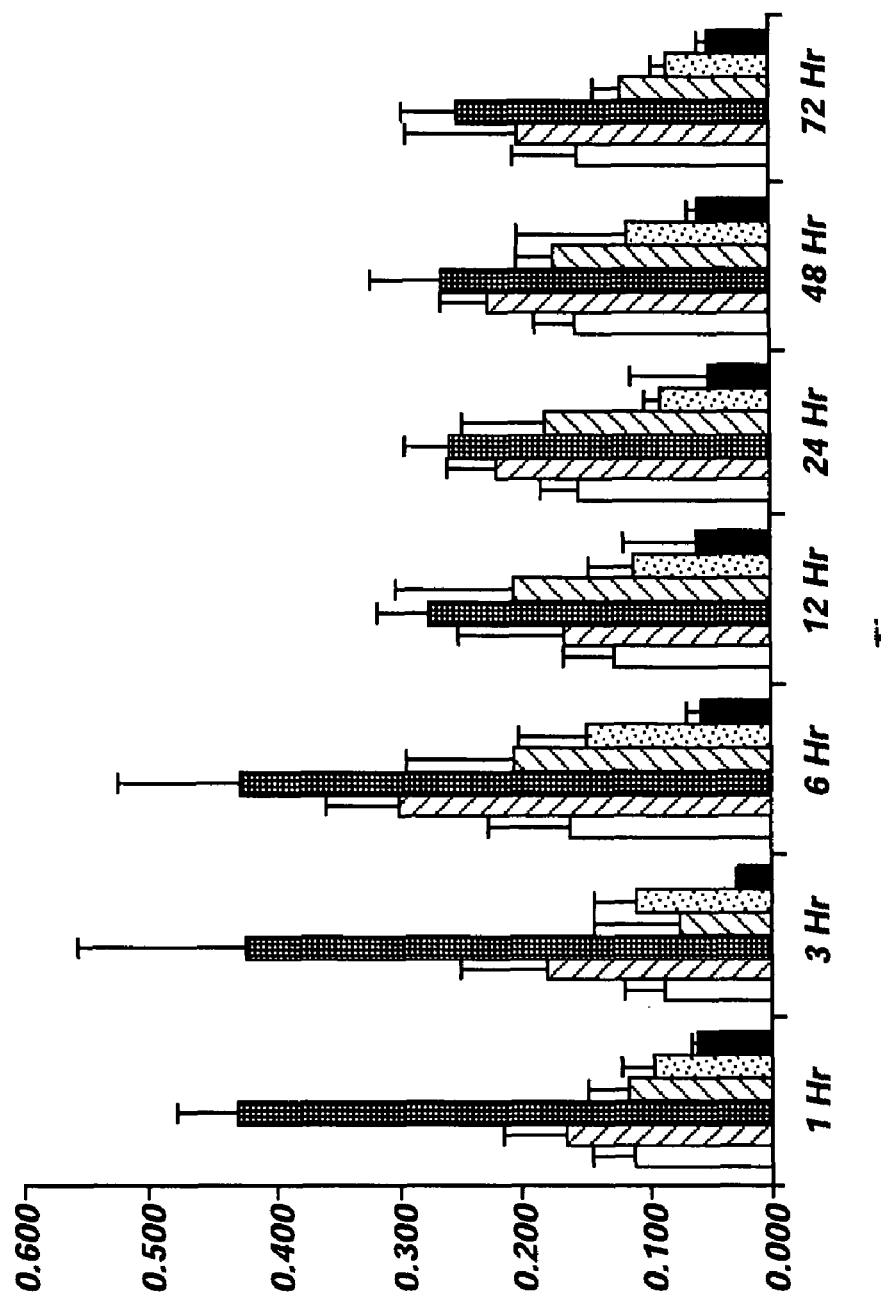
FIG. 13 shows in vivo biodistribution of pORF-mIL-12elasti/EMA; data reported as mean±SD, n=5.

The data suggest localization of the LPC-T/pORF-mIL-12elasti complexes in the lung following systemic administration. These levels were expected as the enhanced permeation and retention (EPR) effect due to the pulmonary metastases would result in higher levels in the lungs due to leaky vasculature and impaired lymphatic drainage. This passive targeting of the complexes allows for increased mIL-12 expression from the local tumor cells resulting from the induced pulmonary metastases. Both FIGS. 12 and 13 represent biodistribution data beginning at day 5 post-injection of the Renca cells. It would be expected that the levels between the tissues to shift to even higher levels in the lungs at later time points following induction of pulmonary metastases. Micro pulmonary metastases would be present, however, they would not be visible to the naked eye. FIG. 12 5.1 shows high levels in the lung up to 3 hrs post-injection of the labeled complexes. At some point between 3 hrs-6 hrs, the LPC-T carrier moves to the kidneys for clearance, which is explained by its high intrinsic water solubility. As for FIG. 13, the levels of the pORF-mIL-12elasti/EMA remain high in the lung up to 6 hrs post-injection. The difference between the LPC-T/BODIPY and pORF-mIL-12elasti/EMA at the 6 hr timepoint suggest separation of the LPC-T/pmIL-12e complexes. Following endocytosis and subsequent pH buffering resulting in release into the cytosolic compartment, the LPC-T would be exocytosed while the pORF-mIL-12elasti would be able to enter through the nuclear pore complexes with subsequent episomal pDNA expression of the therapeutic heterodimer, mIL-12 p70. The exocytosed LPC-T would be removed from the systemic circulation by the reticuloendothelial system (RES) primarily through the kidneys due to its high water solubility. In addition, levels in the liver jump for the LPC-T/BODIPY units following the 3 hr timepoint with transitory levels of the pmIL-12e/EMA in the liver following 6 hrs post-injection.

Example 15

Figure 14:
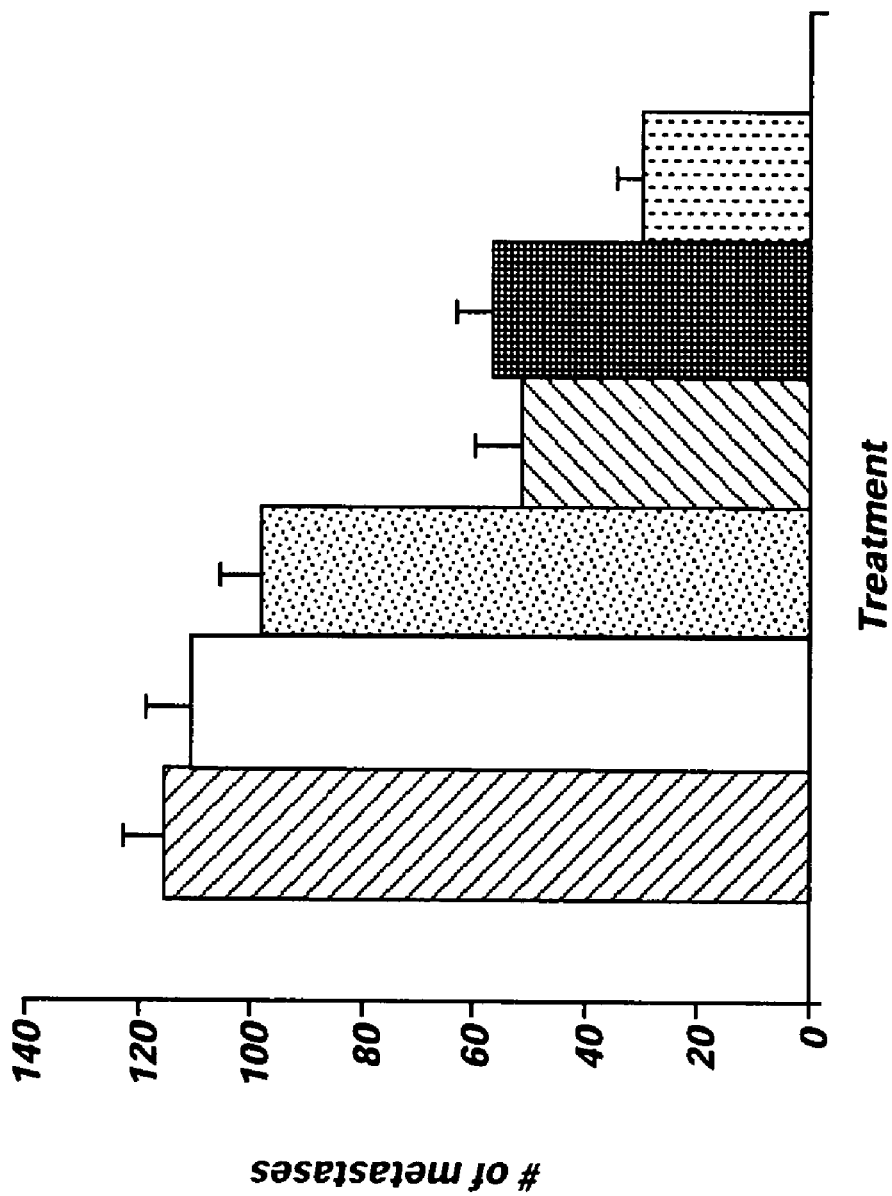
FIG. 14 shows pulmonary metastases data following treatment of induced pulmonary metastases by Renca cells; data reported as mean±SD (* p<0.001 for LPC-T compared to all other groups).

Knowing that the levels in the pulmonary tissue are highest for both the LPC-T gene carrier and therapeutic plasmid pmIL-12e, the effects on lowering the number of pulmonary metastases were determined. As described in Example 14, 6-week old female BALB/c mice were injected through the tail vein with $10^5$ Renca cells to induce pulmonary metastases. As the lungs are the first site of capillary beds, the cancerous cells would become entrapped and localized in the pulmonary tissue with subsequent tumor growth. Treatments of the mice began at day 5 following the induction of pulmonary metastases. Mice were injected with 20 µg pDNA including a PCMS-EGFP negative control and naked pmIL-12e. In addition, naked pmIL-12e was used a control although its efficacy was expected to be minimal due to endogenous nuclease activity. Moreover, LPEI Mw 25 k, BPEI Mw 25 k, and LPC-T Mw 25 k were evaluated for treatment of pulmonary metastases with 20 µg of pmIL-12e. Mice were weighed every 3-4 days to track effects upon the normal activity of the mice with the induced pulmonary metastases. The mice with the LPC-T gene carrier showed increased weight gain during the course of the study suggesting that the efficacy of this treatment may have an additive effect upon the state of the animals. Injections were given on a weekly basis and the study was halted at day 28, whereupon the animals were euthanized using a $Co_2$ chamber and the lungs were harvested. The lungs were fixed in Fekete's solution and injected with Coomassie Blue in order to illuminate the pulmonary metastases. As tumor cells commonly increase local vasculature to themselves, levels of the dye would increase for areas of metastases. The metastatic sites were visualized using a Chemi-Doc system (BioRad Laboratories) and the sites were counted under magnification (FIG. 14). In addition, visible metastatic sites were counted for each of the groups (Table 2). Typically, these visible tumor sites were of ~1 cm in diameter. FIG. 14 shows the effects of the various treatment regimens administered to the diseased mice. As expected the naked pmIL-12e group showed levels of pulmonary metastases consistent with that of the negative control, due to the high levels of endogenous nucleases. Without sufficient protection of the therapeutic plasmid, the levels of therapeutic mIL-12 produced would be minimal at best. Next, two LPEI controls were evaluated, one sample with non-therapeutic EGFP (pCMV-EGFP) and the other with therapeutic pmIL-12. It has been established that the mere introduction of polymer/ plasmid complexes (polyplexes) may invoke an immune response; consequently, levels of metastases dropped slightly with the use of the LPEI/pEGFP. The next two groups compared head-to-head LPEI 25 k and BPEI 25 k for the treatment of pulmonary metastases. Levels were not significantly different between the two groups; however, the mice appeared to tolerate the LPEI treatment more than the BPEI treatment based on the weekly tracking of weights. Finally, LPC-T showed the lowest levels of pulmonary metastases compared to any of the groups and was statistically significant ($p<0.001$) when compared to all the other groups in this study. The lower toxicity and increased transgene expression that was apparent in vitro were quite visible with the number of pulmonary metastases inhibited by systemic administration of LPC-T/pORF-mIL-12elasti. Approximately 67% of the pulmonary metastases that appeared with the negative control were no longer visible with the LPC-T/pORF-mIL-12elasti treatment. Moreover, in a stark example of the increased efficacy over BPEI, LPC-T/pORF-mIL-12e was nearly 50% more effective than BPEI/pORF-mIL-12e or LPEI/pORF-mIL-12e in decreasing the number of pulmonary metastases. It should be noted that mice were treated with 20 μg pORF-mIL-12, which allows for increased plasmid dosage in future studies. The LPC-T/pmIL-12e formulation was the best-tolerated systemic administration modality of all the groups. The mice gained weight in a nearly linear fashion over the ~35 day study. From these results it was concluded that LPC-T was an effective carrier of pORF-mIL-12elasti for passive targeting of the pulmonary tissue following systemic injection.

TABLE 2

| Treatment | Average No. Visible Metastases |
| --- | --- |
| C- | 8 |
| Naked pORF-mIL-12elasti | 7 |
| LPEI/pEGFP | 6 |
| LPEI/pORF-mIL-12elasti | 6 |
| BPEI/pORF-mIL-12elasti | 4 |
| LPC-T/pORF-mIL-12elasti | 1 |

Example 16

The LPC-T gene carrier was initially designed for treatment by systemic administration; however, based upon the favorable in vitro characteristics including particle size, zeta potential, and water solubility, LPC-T was evaluated for treatment of subcutaneous tumors. As previously detailed, 6-week old female BALB/c mice were subcutaneously injected in the right flank with $10^5$ Renca cells. Small subcutaneous tumors were detected by day −10 and progressively grew reaching a maximum size of ~600 mm$^3$. The treatments began on day −20 with weekly local (peritumoral) injections of complexes in 200 μL total volume. The size of the tumors were measured using calibrated calipers every 3-4 days and the tumor volume was calculated as $0.5 \times a \times b^2$, where "a" is the length by the long axis and "b" is the length of the short axis. Larger tumors became ulcerative and necrotic well towards the end of the LPC-T/pORF-mIL-12elasti SC study. Mice surviving by day 22 of therapeutic injections were sacrificed and evaluated for metastases from the subcutaneous site; however, no metastases were seen in the heart, liver, lungs, kidney, or spleen. LPC-T/pORF-mIL-12e treated mice exhibited some tumor regression beginning at day 10 that proceeded for the next 12 days; however, LPEI/pmIL-12e showed an increase in tumor growth above that of the negative controls on days 15 and day 19. It is difficult to explain this trend, but the number of animals is low (n=4) and the standard deviations are broad on days 15 and 19. Perhaps the LPEI induces a transient toxicity response as shown by the deaths of two animals during this interval. Needless to say, LPC-T and LPEI injected systemically or locally are more easily tolerated by mice, further confirming that the decreased cationic charge density of LPEI would provide a higher safety profile, decreased toxicity, and increased survival.

The subject matter claimed is:

1. A method comprising reacting a linear polyethylenimine having an average molecular weight of about 423 to about 50,000 and comprising a terminal hydroxyl group with a chloroformate ester of a sterol comprising a 3-ol group, thereby resulting in a linear polyethylenimine sterol conjugate comprising the sterol covalently bonded to the terminal hydroxyl group wherein the linear polyethylene sterol conjugate has a formula represented by

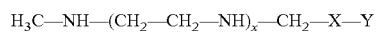

wherein x is an integer of about 8 to about 1,200, X is —O—CO—, and Y is a residue of the sterol comprising a 3-ol group.

2. The method of claim 1 wherein the sterol is selected from cholesterol, cholestanol, coprosterol, epicholestanol, epicholesterol, ergostanol, α-ergostenol, β-ergostenol, γ-ergostenol, ergosterol, 22,23-dihydroergosterol, stigmasterol, stigmastanol, (3β)-7-dehydrocholesterol, desmosterol, allocholesterol, 24-hydroxycholesterol, 25-hydroxycholesterol, campesterol, $\alpha_1$-sitosterol, β-sitosterol, γ-sitosterol, lumisterol, pyrocalciferol, isopyrocalciferol, azacosterol, neoergosterol, and dehydroergosterol.

3. The method of claim 1 wherein the sterol comprises cholesterol.

4. A method comprising:
   (a) reacting a linear polyethylenimine having an average molecular weight of about 423 to about 50,000 and comprising a terminal hydroxyl group and a plurality of secondary amine nitrogen atoms with a protecting reagent such that the protecting reagent bonds with the terminal hydroxyl group, resulting in a protected linear polyethylenimine;
   (b) reacting a chloroformate ester of a sterol comprising a 3-ol group with the protected linear polyethylenimine such that the chloroformate ester of a sterol bonds with at least one of the plurality of secondary amine nitrogen atoms, resulting in a protected linear polyethylenimine sterol conjugate; and
   (c) deprotecting the protected linear polyethylenimine sterol conjugate with a deprotecting reagent, resulting in a linear polyethylenimine sterol conjugate, wherein the linear polyethylene sterol conjugate has a formula represented by

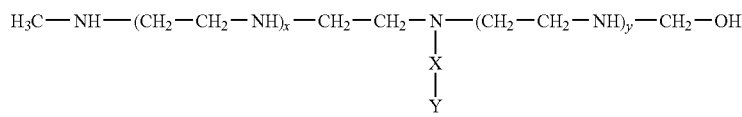

wherein x is an integer of about 0 to about 1,200, y is an integer of about 0 to about 1,200, with the proviso that x+y is about 8 to about 1,200, X is —CO—, and Y is a residue of the sterol comprising a 3-ol group.

5. The method of claim 4 wherein the sterol is selected from cholesterol, cholestanol, coprosterol, epicholestanol, epicholesterol, ergostanol, α-ergostenol, β-ergostenol, γ-ergostenol, ergosterol, 22,23-dihydroergosterol, stigmasterol, stigmastanol, (3β)-7-dehydrocholesterol, desmosterol, allocholesterol, 24-hydroxycholesterol, 25-hydroxycholesterol, campesterol, $\alpha_1$-sitosterol, β-sitosterol, γ-sitosterol, lumisterol, pyrocalciferol, isopyrocalciferol, azacosterol, neoergosterol, and dehydroergosterol.

6. The method of claim 4 wherein the sterol comprises cholesterol.

7. The method of claim 4 wherein the protecting reagent comprises chlorotrimethylsilane and the protected linear polyethylenimine comprises linear polyethylenimine trimethyl silane.

8. The method of claim 7 wherein the deprotecting reagent comprises trifluoroacetic acid.

9. A method comprising reacting a linear polyethylenimine having an average molecular weight of about 423 to about 50,000 and comprising a terminal hydroxyl group and a plurality of secondary amine nitrogen atoms with a chloroformate ester of a sterol comprising a 3-ol group such that the chloroformate ester of the sterol bonds with the terminal hydroxyl group and at least one of the plurality of secondary amine nitrogen atoms, thereby resulting in a linear polyethylenimine sterol conjugate.

10. The method of claim 9 wherein the sterol is selected from cholesterol, cholestanol, coprosterol, epicholestanol, epicholesterol, ergostanol, α-ergostenol, β-ergostenol, γ-ergostenol, ergosterol, 22,23-dihydroergosterol, stigmastanol, stigmastanol, (3β)-7-dehydrocholesterol, desmosterol, allocholesterol, 24-hydroxycholesterol, 25-hydroxycholesterol, campesterol, $\alpha_1$-sitosterol, β-sitosterol, γ-sitosterol, lumisterol, pyrocalciferol, isopyrocalciferol, azacosterol, neoergosterol, and dehydroergosterol.

11. The method of claim 9 wherein the sterol comprises cholesterol.

12. The method of claim 9 wherein, the linear polyethylenimine sterol conjugate has a formula represented by

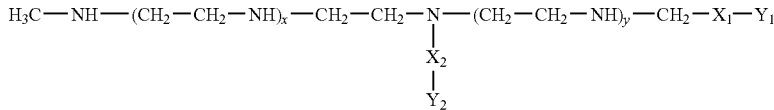

wherein x is an integer of about 0 to about 1,200, y is an integer of about 0 to about 1,200, with the proviso that x+y is about 8 to about 1,200, $X_1$ and $X_2$ are —O—CO— and —CO—, respectively, and $Y_1$ and $Y_2$ are residues of the sterol comprising a 3-ol group.

13. A method of delivering a nucleic acid into a mammalian cell comprising:
(a) mixing the nucleic acid with a linear polyethylenimine sterol conjugate to result in a complex, wherein the linear polyethylenimine sterol conjugate has a formula represented by

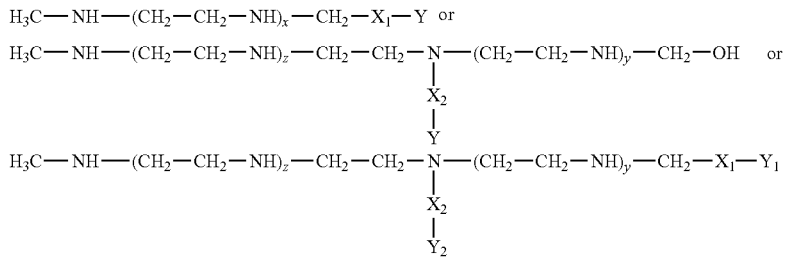

wherein x is an integer of about 8 to about 1,200, y is an integer of about 0 to about 1,200, and z is an integer of about 0 to about 1,200, with the proviso that z+y is about 8 to about 1,200, $X_1$ is —O—CO—, $X_2$ is —CO—, and $Y_1$ and $Y_2$ are residues of a sterol comprising a 3-ol group; and
(b) contacting the mammalian cell with the complex such that the complex enters the mammalian cell, thereby delivering the nucleic acid into the mammalian cell.

14. The method of claim 13 wherein the linear polyethylenimine sterol conjugate has a formula represented by

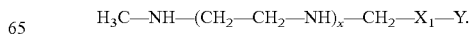

15. The method of claim 13 wherein the linear polyethylenimine sterol conjugate has a formula represented by

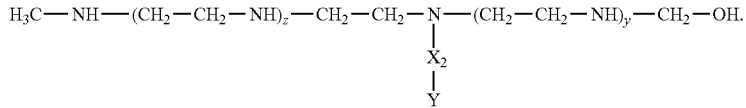

16. The method of claim 13 wherein the linear polyethylenimine sterol conjugate has a formula represented by

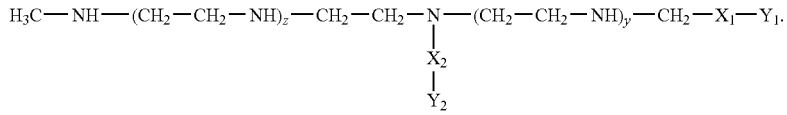

17. The method of claim 13 wherein the sterol is selected from cholesterol, cholestanol, coprosterol, epicholestanol, epicholesterol, ergostanol, α-ergostenol, β-ergostenol, γ-ergostenol, ergosterol, 22,23-dihydroergosterol, stigmasterol, stigmastanol, (3β)-7-dehydrocholesterol, desmosterol, allocholesterol, 24-hydroxycholesterol, 25-hydroxycholesterol, campesterol, $\alpha_1$-sitosterol, β-sitosterol, γ-sitosterol, lumisterol, pyrocalciferol, isopyrocalciferol, azacosterol, neoergosterol, and dehydroergosterol.

18. The method of claim 13 wherein the sterol comprises cholesterol.

* * * * *